United States Patent
Cui et al.

(10) Patent No.: US 10,786,573 B2
(45) Date of Patent: Sep. 29, 2020

(54) CONDUCTIVE POLYMER GRAPHENE OXIDE COMPOSITE MATERIALS

(71) Applicants: University of Pittsburgh—Of The Commonwealth System of Higher Education, Pittsburgh, PA (US); Xinyan Cui, Wexford, PA (US); Xiliang Luo, Qingdao (CN); Cassandra Weaver, Pittsburgh, PA (US)

(72) Inventors: Xinyan Cui, Wexford, PA (US); Xiliang Luo, Qingdao (CN); Cassandra Weaver, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 339 days.

(21) Appl. No.: 14/433,389

(22) PCT Filed: Oct. 4, 2013

(86) PCT No.: PCT/US2013/063421
§ 371 (c)(1),
(2) Date: Apr. 3, 2015

(87) PCT Pub. No.: WO2014/055846
PCT Pub. Date: Apr. 10, 2014

(65) Prior Publication Data
US 2015/0246128 A1    Sep. 3, 2015

Related U.S. Application Data

(60) Provisional application No. 61/709,639, filed on Oct. 4, 2012.

(51) Int. Cl.
*A61K 47/02* (2006.01)
*A61K 47/34* (2017.01)
(Continued)

(52) U.S. Cl.
CPC ............ *A61K 47/02* (2013.01); *A61K 9/0009* (2013.01); *A61K 9/7007* (2013.01);
(Continued)

(58) Field of Classification Search
None
See application file for complete search history.

(56) References Cited

U.S. PATENT DOCUMENTS

2009/0087493 A1   4/2009   Dai
2011/0227000 A1   9/2011   Ruoff
2013/0266628 A1*  10/2013  Thalappil ............... B82Y 30/00
                                                          424/409

FOREIGN PATENT DOCUMENTS

WO    WO2012109473 A2    8/2012
WO    WO2014055846       4/2014

OTHER PUBLICATIONS

Abidian et al ("Conducting-Polymer Nanotubes for Controlled Drug Release," Adv. Mater. 2006, 18, 405-409 (2006)).*
(Continued)

*Primary Examiner* — Nicole P Babson
(74) *Attorney, Agent, or Firm* — Bartony & Associates, LLC.

(57) ABSTRACT

A composition includes a composite material including at least one conducting polymer doped with graphene oxide and at least one agent immobilized at least one of (i) on graphene oxide extending from the surface of the composite material or (ii) within the composite material.

20 Claims, 10 Drawing Sheets

(51) Int. Cl.
*A61K 31/573* (2006.01)
*A61K 38/39* (2006.01)
*A61K 45/06* (2006.01)
*A61K 9/70* (2006.01)
*A61K 9/00* (2006.01)
*A61K 47/52* (2017.01)
*A61N 1/04* (2006.01)

(52) U.S. Cl.
CPC ............ *A61K 31/573* (2013.01); *A61K 38/39* (2013.01); *A61K 45/06* (2013.01); *A61K 47/34* (2013.01); *A61K 47/52* (2017.08); *A61N 1/0428* (2013.01)

(56) References Cited

OTHER PUBLICATIONS

Rozlosnik et al ("New directions in medical biosensors employing poly(3,4-ethylenedioxythiophene) derivative-based electrodes," Anal Bioanal Chem (2009) 395: 637m, online Jul. 31, 2009).*

Ahuja et al ("Biomolecular immobilization on conducting polymers for biosensing applications," vol. 28, Issue 5, Feb. 2007, pp. 791-805).*

Wan et al ("Ionic conductivity of chitosan membranes," Polymer 44 (2003) 1057-1065).* https://www.merriam-webster.com/dictionary/dopant.*

Wan et al. "Ionic conductivity of chitosan membranes" Polymer 44. 1057-1065 (Year: 2003).* https://www.merriam-webster.com/dictionary/dopant (Year: 2017).*

Zhu. Y. et al.,Graphene and Graphene Oxide: Synthesis, Properties, and Applications, Advanced Materials, 2010, vol. 22, pp. 3906-3924.

Hummers, W. S. and Offeman, R. E., Preparation of Graphitic Oxide, J Am Chem Soc, 80, 1339-1339 (1958).

Mohanty, N. and Berry, V., Graphene-Based Single-Bacterium Resolution Biodevice and DNA transistor: Interfacing Graphene Derivatives with Nanoscale and Microscale Biocomponents, Nano Lett, 2008, 8, 4469-4476.

NeuronJ plugin for Image—http://rsbweb.nih.gov/ij/docs/concepts.html.

Wang, H. L. et al.Graphene oxide doped polyaniline for supercapacitors. Electrochem Commun 2009, 11, (6), 1158-1161.

* cited by examiner

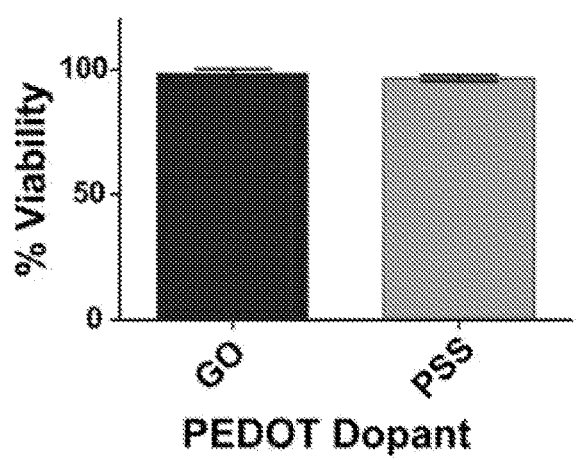
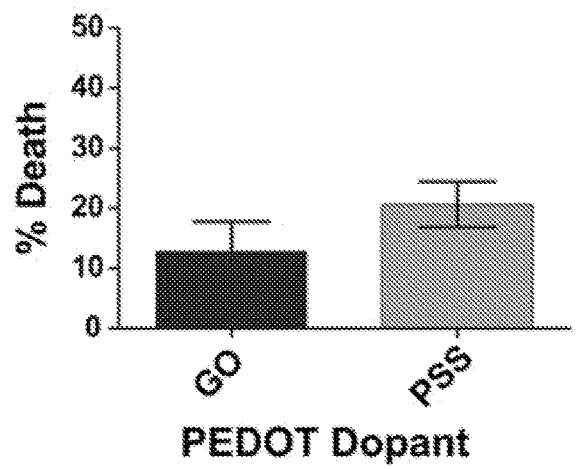
Fig. 3A    Fig. 3B
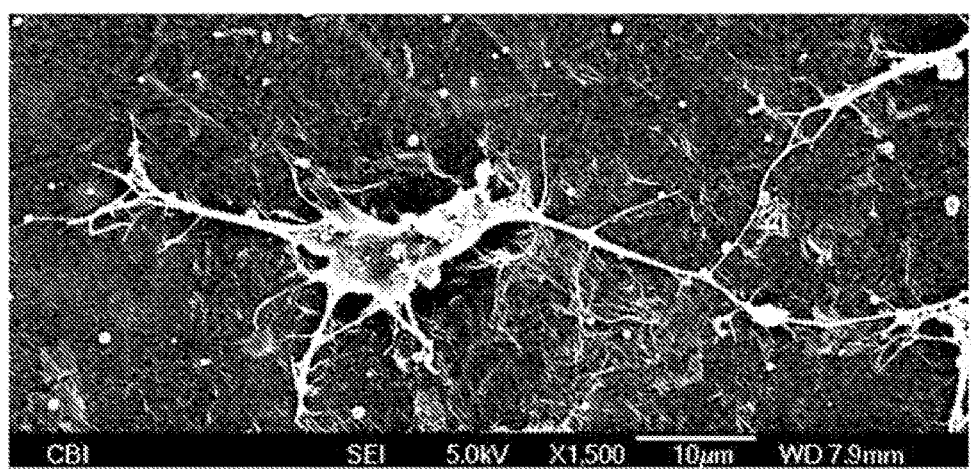
Fig. 4

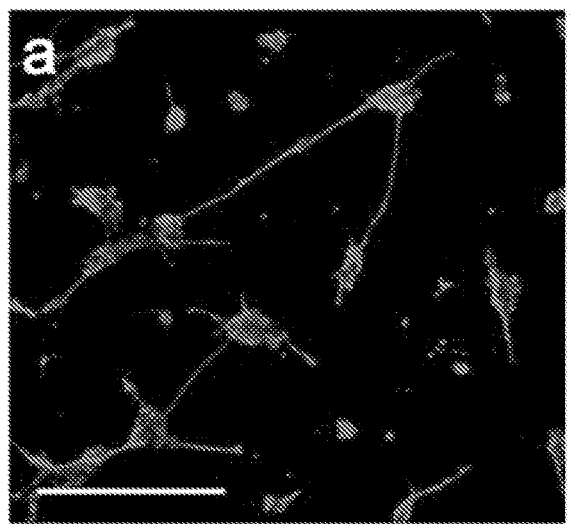
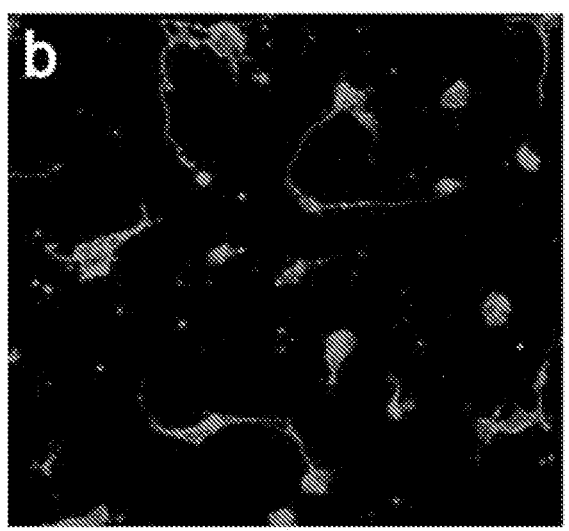
Fig. 5A  Fig. 5B
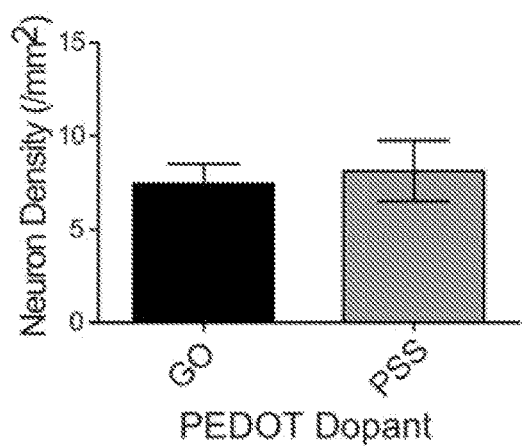
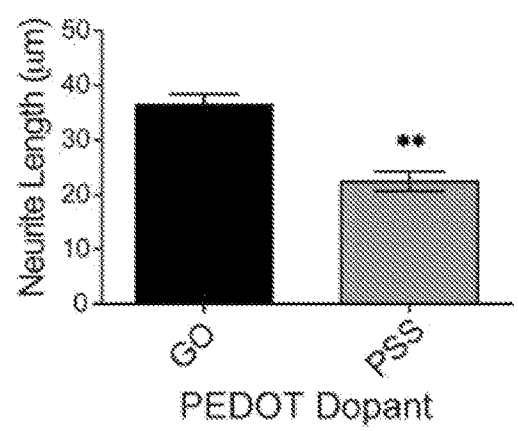
Fig. 5C  Fig. 5D

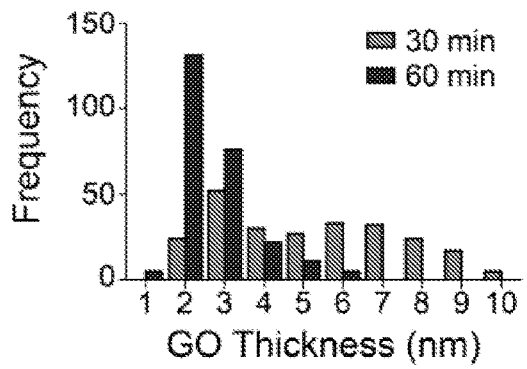
Fig. 11A
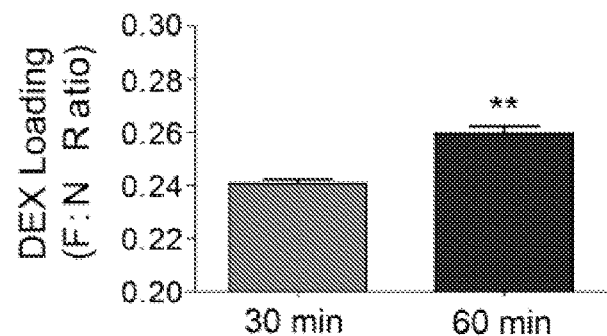
Fig. 11C
Fig. 11B
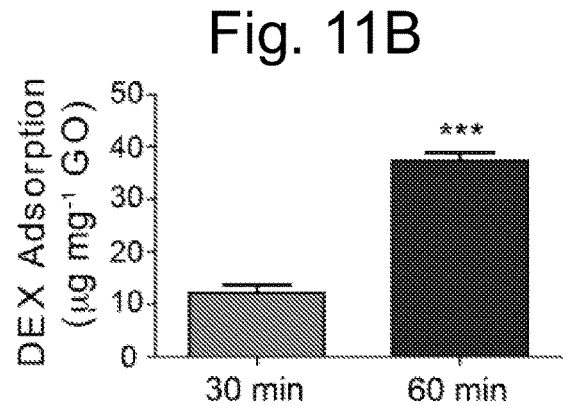
Fig. 11D
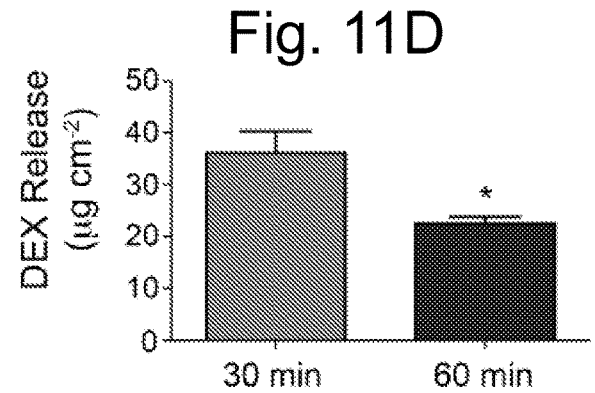
Fig. 11E
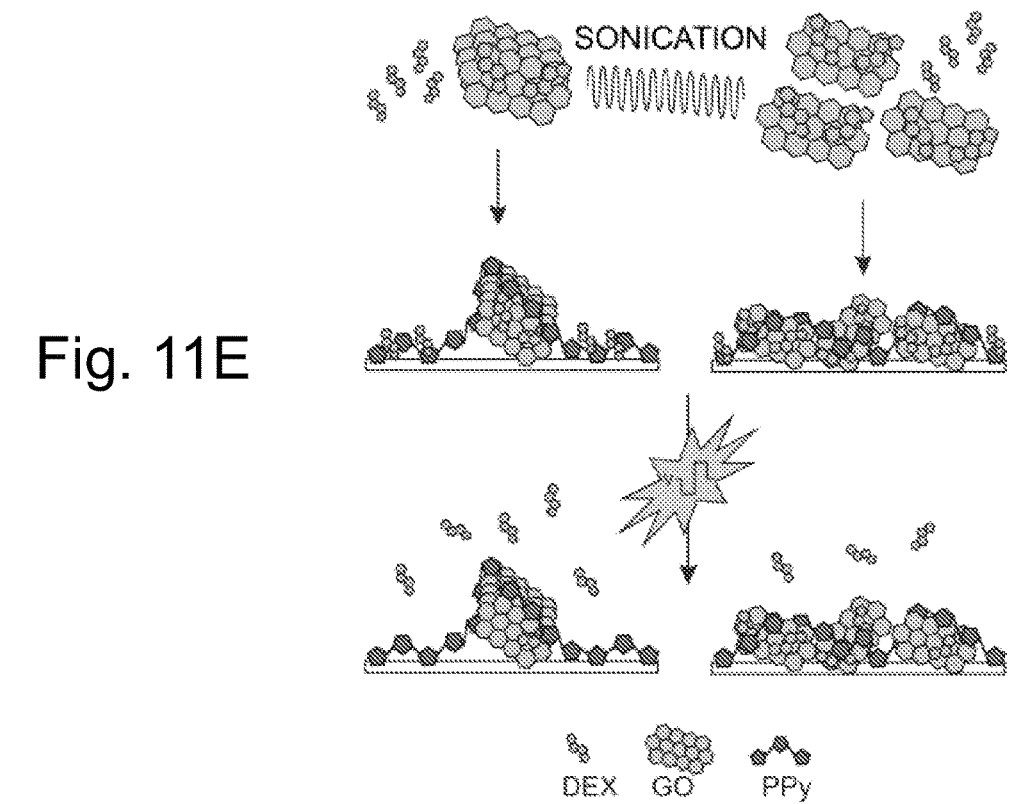

Fig. 12A     Fig. 12B
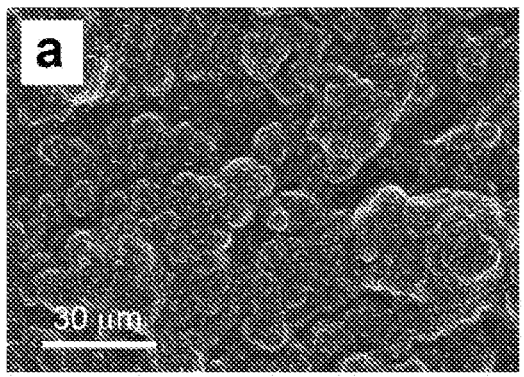
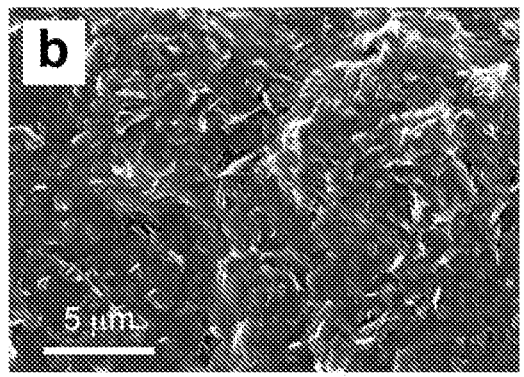
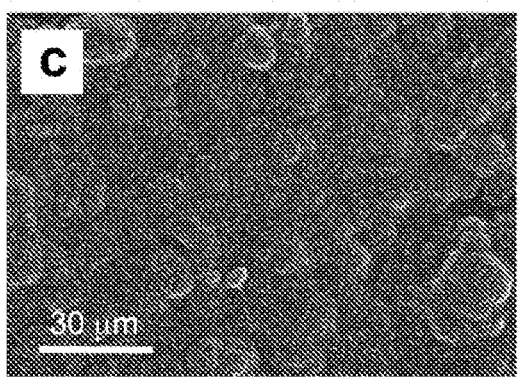
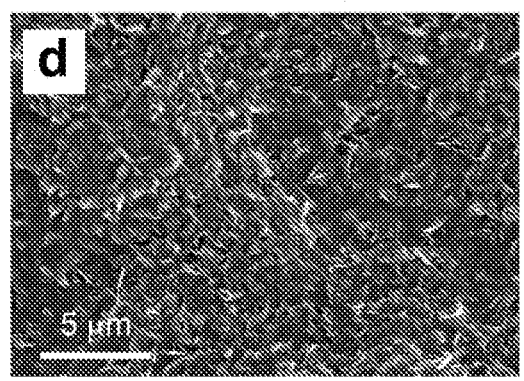
Fig. 12C     Fig. 12D

CONDUCTIVE POLYMER GRAPHENE OXIDE COMPOSITE MATERIALS

CROSS-REFERENCE TO RELATED APPLICATION

This application is a national phase filing of PCT International Patent Application No. PCT/US2013/063421, filed Oct. 4, 2013, which claims benefit of U.S. Provisional Patent Application Ser. No. 61/709,639, filed Oct. 4, 2012, the disclosures of which are incorporated herein by reference.

GOVERNMENTAL INTEREST

This invention was made with government support under grant nos. 0748001 and 0729869 awarded by the National Science Foundation and grant no. R01NS062019 awarded by the National Institutes of Health. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

With advances in the preparation and characterization of graphene and graphene oxide (GO), there has been growing interest in those materials because of their outstanding electrical, physical and chemical properties. The application of graphene and GO for interacting with biological systems has only been recently explored. To date, studies evaluating the biocompatibility of graphene and GO have been inconclusive, with some reports demonstrating severe dose-dependent toxicity, while others indicate that graphene nanomaterials may enhance cell growth.

Another class of conductive organic material, conducting polymers (sometimes referred to herein as CP), has been extensively studied in biological and biomedical fields such as biosensors, neural tissue engineering and neural electrodes. In these applications, it may be desired to immobilize biologically active agents such as biomolecules to the polymer to impart functionalities specific for interfacing with the biological systems. Such modification often requires the substrate material to have at least one derivatizable functional group, which many of the conducting polymers, such as polyethylenedioxythiophene (PEDOT), lack. To add functional groups to a conducting polymer such as PEDOT, generally two strategies have been adopted. Using PEDOT as an example, one strategy is the direct addition of functional groups to the monomer 3,4-ethylenedioxythiophene (EDOT), followed by polymerization of the modified EDOT monomer. This method requires tedious synthesis and purification procedures for the modified EDOT monomers, and the added functional groups may pose electronic and steric limitations during polymerization. Once again, using PEDOT as an example, the other strategy is the copolymerization of EDOT with other monomers or molecules that possess functional groups. Although fairly simple, this method is still unsatisfactory because the presence of these molecules may impair the conductivity and stability of the resultant PEDOT.

Another method of imparting bioactive functionality to a conductive polymer such as PEDOT is to dope the polymer with bioactive molecules directly. Peptides, drugs and proteins have been directly incorporated in PEDOT for neural interfacing or controlled drug delivery. However, only negatively charged biomolecules can be used as dopants and most of them are poor dopants because of their weak charge and large size. Poor dopants lead to difficulty in electropolymerization and low conductivity of the resulting polymer. Furthermore, the biomolecules are entrapped throughout the film, limiting the exposure of the functional domain at the surface.

SUMMARY

In one aspect, a composition includes a composite material including at least one conducting polymer doped with graphene oxide and at least one agent immobilized at least one of (i) on graphene oxide extending from the surface of the composite material or (ii) within the composite material. In a number of embodiments, the at least one agent is immobilized on graphene oxide extending from the surface of the composite material. The at least one agent may, for example, be chemically bonded to the graphene oxide or adsorbed on the graphene oxide. In a number of embodiments, the at least one agent is covalently bonded or ionically bonded to the graphene oxide.

In a number of embodiments, the at least one agent is releasably immobilized within the composite material. The at least one agent may, for example, be controllably released from within the composition via application of electrical energy thereto.

The at least one agent may, for example, be an anionic agent, a cationic agent, a zwitterionic agent or a neutral agent. In a number of embodiments, the at least one agent is a biologically active agent. The biologically active agent may, for example, include or be at least one of a biomolecule or a drug.

The biologically active agent may, for example, include or be an amphetamine, a steroid, an anesthetic, an analgesic, an antacid, an antibiotic, an anticoagulant, an antidepressant, an antidote, an antihistamine, an anti-inflammatory, an antimycotic, an anticancer agent, an analgesic agent, an antirejection agent, an antiretroviral, an antiviral, a barbiturate, a beta blocker, a booster, a contraceptive, a decongestant, a depressant, an emetic, an expectorant, a hypnotic, an immunosuppressant, a laxative, a narcotic, a neurochemical, an opiates, a painkiller, a prophylactic, a purgative, a relaxant, a sedative, a statin, a suppressant, a tranquilizer, a vaccine or a vitamin.

In a number of embodiments, the biologically active agent is or includes a superoxide dismutase mimic, a porphyrin, a protein, an organic catalyst, a nucleic acid, an organometallic, a glycoprotein, a glycosaminoglycan, a peptide, an aptamer, a polyamine, a polyamino acid, a cytokine, a carbohydrate, an oleophobic, a lipid, extracellular matrix, a component of extracellular matrix, a growth factor, a hemostatic agent, a virus, a vireno, a virus vector, or a prion. In a number of embodiments, the biologically active agent is or include a cell adhesion molecule, an adhesive protein, a peptide, a cytokine or a growth factor. In a number of embodiments, the biologically active agent is or includes an aptamer, an antibody, an enzyme, a ribozyme, DNA or RNA. The biologically active agent may, for example, be dexamethasone.

In general, any conductive polymer is suitable for use herein. In a number of embodiments, the at least one conductive polymer is selected from the groups of polypyrroles, polyanilines, poly(3,4-ethylenedioxythiophene), poly(fluorine)s, polypyrenes, polyazulenes, polynaphthalenes, polycarbazoles, polyindoles, polyazepines, poly(p-phenylene sulfide), polythiophenes, poly p-(phenylene vinylene), poly p-phenylene, and their derivatives.

In another aspect, a system includes a support and a composition as described above deposited upon the support. In a number of embodiments, the support is an electrode. As described above, the composition comprising a composite material comprising at least one conducting polymer doped with graphene oxide, and at least one agent immobilized at least one of (i) on graphene oxide extending from the surface of the composite material or (ii) within the composite material. The at least one agent may, for example, be as described above. Electrical circuitry or electronics may, for example, be in electrical connection with the electrode to, for example, effect control, processing, analysis etc.

In a number of embodiments, the system is operable as a sensor for detecting an analyte. The at least one agent may, for example, selectively interact with the analyte. In a number of embodiments, the at least one agent is a biologically active agent as described above. In a number of embodiments, the biologically active agent is or includes a superoxide dismutase mimic, a porphyrin, a protein, an organic catalyst, a nucleic acid, an organometallic, a glycoprotein, a glycosaminoglycan, a peptide, an aptamer, a polyamine, a polyamino acid, a cytokine, a carbohydrate, an oleophobic, a lipid, extracellular matrix, a component of extracellular matrix, a growth factor, a hemostatic agent, a virus, a vireno, a virus vector, or a prion. In a number of embodiments of sensor system hereof, the biologically active agent is or includes a cell adhesion molecule, an adhesive protein, a peptide, a cytokine or a growth factor. In a number of embodiments of sensor systems hereof, the biologically active agent is or includes a superoxide dismutase mimic, an aptamer, an antibody, a protein such as an enzyme, or a nucleic acid such as a ribozyme, DNA or RNA.

In general, any conductive polymer is suitable for use in sensors hereof. In a number of embodiments, the at least one conductive polymer is selected from the groups of polypyrroles, polyanilines, poly(3,4-ethylenedioxythiophene), poly(fluorine)s, polypyrenes, polyazulenes, polynaphthalenes, polycarbazoles, polyindoles, polyazepines, poly(p-phenylene sulfide), polythiophenes, poly p-(phenylene vinylene), poly p-phenylene, and their derivatives.

In a number of embodiments, the system is operable to controllably release the at least one agent which is immobilized within the composite material. In a number of embodiments, the at least one agent is a bioactive agent as described above. The bioactive agent may, for example, be or include a drug. The drug may, for example, be an amphetamine, a steroid, an anesthetic, an analgesic, an antacid, an antibiotic, an anticoagulant, an antidepressant, an antidote, an antihistamine, an anti-inflammatory, an antimycotic, an anticancer agent, an analgesic agent, an antirejection agent, an antiretroviral, an antivirals, a barbiturate, a beta blocker, a booster, a contraceptive, a decongestant, a depressant, an emetic, an expectorant, a hypnotic, an immunosuppressant, a laxative, a narcotic, a neurochemical, an opiates, a painkiller, a prophylactic, a purgative, a relaxant, a sedative, a statin, a suppressant, a tranquilizer, a vaccine or a vitamin.

In another aspect, a method of forming a composition includes forming a composite material including at least one conducting polymer and graphene oxide, wherein at least a portion of the graphene oxide extends from a surface of the composite material. The composite material may, for example, be formed by polymerizing at least one conducting polymer in the presence of graphene oxide. In a number of embodiments, the composite is formed by electropolymerizing the at least one conducting polymer in an aqueous solution comprising at least one monomer and graphene oxide. The method further includes immobilizing at least one agent upon graphene oxide extending from the composite material. The at least one agent may, for example, be as described above. In a number of embodiments, the at least one agent is a biologically active agent as described above. The particle size of the graphene oxide may, for example, be used/varied to control physical properties of the compositions. For example, the particle size of the graphene oxide may be used/varied to control at least one of the amount of agent in the composition, one or more electrical properties (for example, conductance, impedance etc.) of the composition, or the morphology of the composition.

In a number of embodiments, the at least one agent selectively interacts with an analyte. The composition may, for example, be adapted for use in a sensor for detecting the analyte.

In another aspect, a method of forming a composition includes immobilizing graphene oxide and at least one agent in at least one conducting polymer. In a number of embodiments, the method includes polymerizing at least one conducting polymer in the presence of graphene oxide and the at least one agent such that the at least one agent and the graphene oxide are immobilized within the conducting polymer. In a number of embodiments, the method includes electropolymerizing the at least one conducting polymer in an aqueous solution including at least one monomer, graphene oxide and the at least one agent such that the at least one agent and the graphene oxide are immobilized within the conducting polymer. The at least one agent may, for example, be releasably immobilized within a composite material comprising the conducting polymer and the graphene oxide. The at least one agent may, for example, be as described above. In a number of embodiments, the at least one agent is a biologically active agent as described above. The particle size of the graphene oxide may, for example, be used/varied to control physical properties of the compositions. For example, the particle size of the graphene oxide may be used/varied to control at least one of the amount of agent in the composition, the rate of release of the agent, one or more electrical properties of the composition, or the morphology of the composition. The at least one agent may, for example, be controllably releasable from the composite material upon application of electrical energy thereto. For example, a biologically active agent such as a drug may be controllably released upon application of electrical energy.

In a further aspect, a method includes providing a composition, which includes a composite material comprising at least one conducting polymer doped with graphene oxide and at least one agent releasably immobilized within the composite material, and applying an electric current to the composition to release the agent from the composite material. As described above, in a number of embodiments, the at least one agent is a biologically active agent such as a drug.

In still a further aspect, a method of forming a composition includes immobilizing graphene oxide in at least one conducting polymer and controlling particle size of the graphene oxide to control at least one property of the composition. In a number of embodiments, the method includes polymerizing the at least one conducting polymer in the presence of graphene oxide, and controlling particle size of the graphene oxide to control at least one property of the composition. In a number of embodiments, the method includes electropolymerizing the at least one conducting polymer in an aqueous solution comprising at least one monomer and graphene oxide, and controlling particle size of the graphene oxide to control at least one property of the composition. Particle size of the graphene oxide may, for example, be used, varied or predetermined (for example, to be within a predetermined range of particle size) to control at least one of the amount of an agent in the composition, a rate of release of the agent from the composition, one or more electrical properties of the composition or the morphology of the composition. Control of such properties is useful in, for example, controlling the operation of electrodes, sensors, agent delivery systems, conductors, superconductors, etc. including the composition.

The present devices, systems, methods and compositions, along with the attributes and attendant advantages thereof, will best be appreciated and understood in view of the following detailed description taken in conjunction with the accompanying drawings.

BRIEF DESCRIPTION OF THE DRAWINGS

FIG. 3A illustrates viability of neurons growing on PEDOT films doped with GO or PSS at 24 hours, showing that PEDOT/GO films perform similarly to control PEDOT/PSS films, exhibiting no loss of viability (the error bar represents SEM (n=5)).

FIG. 3B illustrates death of neurons growing on PEDOT films doped with GO or PSS at 24 hours, showing that PEDOT/GO films perform similarly to control PEDOT/PSS films, exhibiting minimal cell death (the error bar represents SEM (n=5)).

FIG. 4 illustrates an SEM image of a neuron growing on the PEDOT/GO surface at 1 day, wherein the cell exhibits extensive neurite branching and forms contacts with other cells, demonstrating the biocompatibility of the PEDOT/GO film.

FIG. 5A illustrates neuron growth on a PEDOT surface doped with GO at 3 days in a representative 20× fluorescent image of β-III-tubulin immunofluorescent reactivity (green) of neurons.

FIG. 5B illustrates neuron growth on a PEDOT surface doped with PSS at 3 days in a representative 20× fluorescent image of β-III-tubulin immunofluorescent reactivity (green) of neurons.

FIG. 5C illustrates neuron density (±SEM, n=3) of cells growing on the polymer surfaces.

FIG. 5D illustrates average neurite length (±SEM, n=3) of cells growing on the polymer surfaces, showing that the GO-doped PEDOT films support neurons with longer neurites extensions than PSS doped PEDOT films (** $p<0.01$).

FIG. 11A illustrates the effect of sonication on GO nanosheet and GO/PPy nanocomposite properties in a histogram of sheet thickness after 30 min and 60 min sonication.

FIG. 11B illustrates the amount of DEX adsorbed by free GO sheets (*** p<0.001; n=3).

FIG. 11C illustrates elemental analysis of DEX-loaded nanocomposite film, wherein the F:N ratio reflects the amount of drug loaded into the film (** p<0.01; n=3).

FIG. 11D illustrates the amount of DEX released from nanocomposite films in response to 100 voltage pulses, showing that less sonication results in a faster release rate (* p<0.05; n=4).

FIG. 11E illustrates a schematic representation of the effect of GO sheet sonication on nanocomposite properties.

FIG. 12A illustrates the effect of GO sonication on GO/PPy film morphology in an SEM image of DEX-loaded GO/PPy films prepared with GO sonicated for 30 minutes, wherein the scale bar in is 30 μm.

FIG. 12B illustrates the effect of GO sonication on GO/PPy film morphology in an SEM image of DEX-loaded GO/PPy films prepared with GO sonicated for 30 minutes, wherein the scale bar in is 5 μm.

FIG. 12C illustrates the effect of GO sonication on GO/PPy film morphology in an SEM image of DEX-loaded GO/PPy films prepared with GO sonicated for 60 minutes, wherein the scale bar in is 30 μm.

FIG. 12D illustrates the effect of GO sonication on GO/PPy film morphology in an SEM image of DEX-loaded GO/PPy films prepared with GO sonicated for 60 minutes, wherein the scale bar in is 5 μm.

DETAILED DESCRIPTION

Figure 1A:
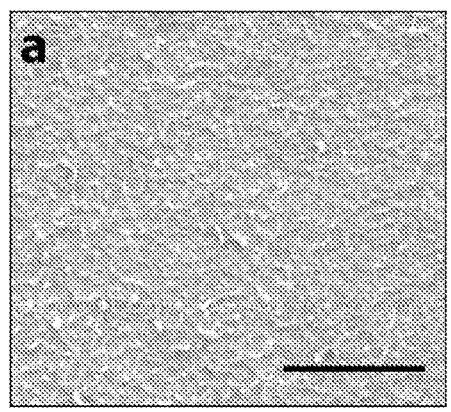
FIG. 1A illustrates an SEM image of a representative, electrodeposited PEDOT/GO film, showing rough, network-like morphology of the surface, wherein the film was electropolymerized at 1.0 V for 600 s in 0.02 M EDOT solution containing 10 mg/mL GO (the scale bar in is 5 µm).

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an agent" includes a plurality of such agents and equivalents thereof known to those skilled in the art, and so forth, and reference to "the agent" is a reference to one or more such agents and equivalents thereof known to those skilled in the art, and so forth.

GO possesses, for example, many oxygen containing functional groups, such as carboxyl, hydroxyl and epoxide, rendering it hydrophilic and dispersible in aqueous solutions. This property, along with its abundance of negatively charged carboxyl groups, makes it an excellent dopant for the electropolymerization of conducting polymers. In addition to electropolymerization, other polymerization techniques as known in the polymer arts may be used. Additionally, GO has recently been shown to act as a promoter of neuronal growth and maturation, making it an interesting candidate as a neural interfacing material. Conducting polymer/GO nanocomposites exhibit favorable electrical properties, energy storage and stability. In a number of embodiments hereof, methods for straightforward electrochemical synthesis of a conductive polymeric material doped with GO are provided. The conductive polymeric materials may be exclusively doped with GO. Unlike some previous GO-containing materials, the GO-doped conductive polymeric materials hereof demonstrate biocompatibility. In a number of representative embodiments, PEDOT was doped with GO, and biocompatibility was demonstrated via in vitro compatibility with neuronal cells.

The GO particles, sheets or nanosheets are partially entrapped by a conductive polymer such PEDOT on the surface of the nanocomposite and many of functional groups such as carboxyl functional groups of GO on the surface are exposed freely. The exposed functional groups of the GO enable immobilizing (via, for example, chemical bonding (for example, covalent or ionic bonding) or via adsorption) of an agent such as biologically active agents (including, for example, biomolecules) to the functional groups of the GO. In a number of representative embodiments, biomolecule decoration on a PEDOT/GO film surface was demonstrated via carbodiimide conjugation. In that regard, in several representative embodiments, covalent immobilization of peptide RNIAEIIKDI (p20), and functional neurite outgrowth domain of extracellular matrix protein, laminin was demonstrated. The immobilization procedures described herein and other straightforward reaction schemes may be universally applied CP/GO composite materials/matrices and bioactive agents (including, for example, bioactive proteins and peptides) for a variety of bio-interfacing and other applications.

Reaction schemes other than carbodiimide conjugation may, for example, be used to chemically bond agents to exposed functional groups of GO in a CP/GO composite material. For example, to react with carboxylic acid group, one may also use $SOCl_2$ to form —CO—Cl which will then react with an amine group of an agent (for example, a protein or a peptide). Moreover, one may also use a biotin-streptavidin linkage. One may also use, for example, hydroxyl or OH functional groups on GO for chemically bonding an agent to GO. For example, silane reagents or gluteraldehyde may be used for coupling to hydroxyl functional groups. Moreover, ionic bonding may also be used.

In a number of embodiments hereof, CP/GO composite materials are used to release agents such a biologically active agent (including, for example, drug molecules) in a controlled manner. A number of representative embodiments hereof demonstrate electrically controlled drug delivery system and methods based on GO nanosheets incorporated into a conducting polymer or CP film. As described above, GO is a two-dimensional nanomaterial composed of a honeycomb carbon lattice structure with functional groups, such as hydroxyl, carboxyl and epoxide functional groups and exhibits exceptional electrical, chemical, and mechanical properties. In a number of representative embodiments hereof, it was demonstrated that when incorporated into polypyrrole (PPy) along with anti-inflammatory drug, dexamethasone (DEX), the GO nanosheets create a stable nanocomposite film that can release the drug molecules on-demand in response to electrical stimulation. Altering, for example, the thickness and size of the GO nanosheets changes the physical properties and release profile of the nanocomposite materials hereof, indicating that such systems may be tuned to the needs of various applications (for example, implementation in therapeutic and exploratory research within the field of biomedicine).

As used herein, the terms "biologically active" or "bioactive" refer generally to an agent, a molecule, or a compound that affects biological or chemical events in a host. Biologically active or bioactive agents may be synthetic molecules, biomolecules, or multimolecular entities and include, but are not limited to, proteins (including, but not limited to, collagen, fibrin/fibrinogen, fibronectin, entactin, tenascin and enzymes (including, but not limited to, MMPs, TIMPs, proteinases, phospholipases, plasmin/plasminogen, lipases, and lysyl oxidase, a crosslinking agent for collagen)), organic catalysts, ribozymes, organometallics, glycoproteins (for example, proteoglycan), glycosaminoglycans (for example, hyaluronic acid or HA), peptides, aptamers, polyamines, polyamino acids, antibodies, nucleic acids, cytokines, carbohydrates, oleophobics, lipids, extracellular matrix and/or its individual components (such as collagen etc.), growth factors, hemostatic agents (including, for example, small molecules such as ATP and epinephrine and derivatives thereof), drugs, pharmaceuticals, chemotherapeutics, and therapeutics. Cells and non-cellular biological entities, such as viruses, virenos, virus vectors, and prions can also be bioactive agents. The term "biomolecule" refers any molecule that is produced by a living organism, including large macromolecules such as proteins, polysaccharides, lipids, and nucleic acids, as well as small molecules such as primary metabolites, secondary metabolites, and natural products.

In a number of embodiments, biologically active agents hereof include, but are not limited to, at least one of a protein, an organic catalyst, a nucleic acid (for example, RNA, DNA, a ribozyme etc.), an organometallic, a glycoprotein, a glycosaminoglycan, a peptide, a polyamine, a polyamino acid, an antibody, a nucleic acid, a steroidal molecule, an antibiotic, an anti-inflammatory, an antiviral, an antimycotic, an anticancer agent, an analgesic agent, an antirejection agent, an immunosuppressant, a cytokine, a carbohydrate, an oleophobic, a lipid, extracellular matrix, an individual component of extracellular matrix, a growth factor, a hemostatic agent, a virus, a vireno, a virus vector or a prion.

In a number of embodiments, the biologically active agent includes extracellular matrix or a component of extracellular matrix. The biologically active agent can also include a hemostatic agent. For example, the biologically active agent can include collagen, fibrin or plasmin. The biologically active agent may, for example, include a hemostatic agent such as a small molecule hemostatic agent (for example, ATP, a derivative of ATP, epinephrine or a derivative of epinephrine).

In several embodiments, the biologically active agent include a growth factor, including, for example, EGF, TGFa, PDGF, VEGF, IGF-1, FGF, HGF, KGF, TGFb, a CXCR3 ligand, IL-10 or IL-4.

In several embodiments, the biologically active agent includes an agent selected to promote at least one of cell adhesion, cell proliferation or cell migration. The biologically active agent can, for example, include sites for binding of at least one of beta1 or beta3 integrins.

In a number of embodiments for directing cell attachment, growth and differentiation, the biologically active agents is a cell adhesion molecule, an adhesive protein, a functional peptide, a cytokine or a growth factor. In a number of embodiments for sensors, the biologically active agent is an aptamer, an antibody, a superoxide dismutase mimic (SODm), an enzyme, a nucleic acid (for example, DNA, RNA or a ribosome). The term "aptamer" refers to oligonucleic acid or peptide molecules that bind to a specific target molecule. Aptamers are excellent biorecognition molecule for biosensors as a result of their high stability, high affinity, and reproducible chemical production. Aptamers of any biomolecular target molecule (or other agents which selectively interact with an analyte) can be readily immobilized on an electrode of any scale (from nano to micro to macro) in the sensors hereof. In that regard, conducting polymer/graphene oxide composite materials are used to facilitate the immobilization of, for example, aptamers on electrodes while enhancing the ability of electrode to detect the analyte by means of electrochemical or electrical measurement. In a number of embodiments, conducting polymers are electrodeposited using graphene oxide as dopants. Functional groups such as carboxylic acid groups of the graphene oxide are then functionalized with an agent (for example, aptamer) of choice.

As used herein, the term "drug" refers to a substance which has an effect (for example, a medicinal, intoxicating, performance enhancing and/or other effects) upon administration to a body of a human or other animal. Medicinal drugs, medicines or pharmaceuticals are chemical substances used in treatment, cure, prevention or diagnosis of diseases or used to otherwise enhance physical or mental well-being. Medicinal drugs include, but are not limited to, amphetamines, steroids, anesthetics (for example, a topical or contact anesthetic), analgesics or painkillers, antacids, antibiotics, anticoagulants, antidepressants, antidotes, antihistamines, anti-inflammatories, antimycotics, antimicrobials (for example, macrolide, a topoisomerase inhibitors or a cephalosporin), anticancer agents, analgesic agents, antirejection agents, antiretrovirals, antivirals, barbiturates, beta blockers, boosters, contraceptives, decongestants, depressants, emetics, expectorants, hypnotics, immunosuppressants, laxatives, narcotics, neurochemicals (neurotransmitters, modulators and inhibitors of neural transmission, agonists and antagonists of ion channels), opiates, prophylactics, purgatives, relaxants, sedatives, statins, suppressants, tranquilizers, vaccines and vitamins.

As used herein, the term "conducting polymer" refers to organic polymer that conduct electricity. Conducting polymers include contiguous $sp^2$ hybridized carbon centers. The polymer chains may, for example, include aromatic cycles and/or double bonds. In general, any conducting polymer(s) can be used herein. Example of suitable conducting polymers include, but are not limited to, polypyrroles, polyanilines, poly(3,4-ethylenedioxythiophene), poly(fluorine)s, polypyrenes, polyazulenes, polynaphthalenes, polycarbazoles, polyindoles, polyazepines, poly(p-phenylene sulfide), polythiophenes, poly p-(phenylene vinylene), poly p-phenylene, and their derivatives.

Figure 1B:
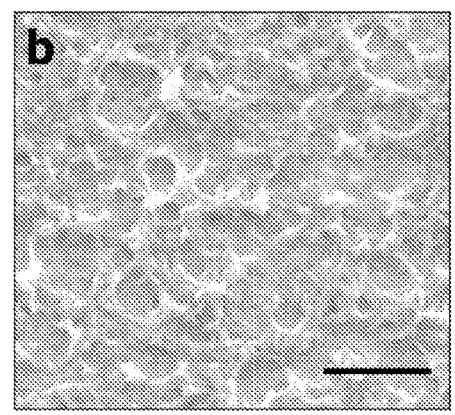
FIG. 1B illustrates an SEM image of the electrodeposited PEDOT/GO film of FIG. 1A wherein the scale bar in is 1 µm.

A number of representative embodiments are discussed below in which an agent is immobilized on exposed graphene oxide (that is, graphene oxide extending from the surface of a CP/GO composite material) or in which an agent is immobilized within the matrix of a CP/GO material. Moreover, various immobilization techniques (including, for example, covalent bonding, ionic bonding, adsorption) are also discussed. Agents may be immobilized in a manner which is relatively resistant to release (for example, via covalent bonding) or in a manner which is conducive to release (for example, via adsorption in certain embodiments). Each of the various manners of immobilizing an agent or agents may, for example, be used exclusively or in combination in various embodiments hereof Immobilization of Agents on Exposed Graphene Oxide GO was synthesized using the modified Hummers method and its micro or nanosheet morphology was confirmed with transmission electron microscopy (TEM). For PEDOT/GO film synthesis in a number of embodiments, electropolymerization of EDOT was carried out in aqueous solution containing only EDOT and GO. In a number of representative examples, no additional electrolyte was used to avoid the involvement of any dopant other than GO. In the presence of the negatively charged GO, EDOT was successfully electropolymerized on the electrode surface, indicating that GO, itself, acts to sufficiently dope the polymer film. In a number of representative embodiments, a GO concentration of 10 mg/ml was utilized to maintain a conductive polymerization solution. In such embodiments, because solutions containing lower amounts of GO resulted in slower or less charge passage during the polymerization reaction, a relatively high concentration of GO was selected to ensure adequate film growth. The resulting film was uniform, and the incorporated GO created a network-like surface morphology (see, for example, FIGS. 1A and 1B). GO concentration may vary over a broad range, however. In a number of embodiment, GO concentrations may, for example, range between approximately 0.5 mg/ml and 20 mg/ml. The particle size of the GO particles/sheet immobilized within a CP matrix hereof may vary broadly. In a number of embodiments, for example, the particles size ranges from 10s of nanometers to 10s of microns.

Figure 1C:
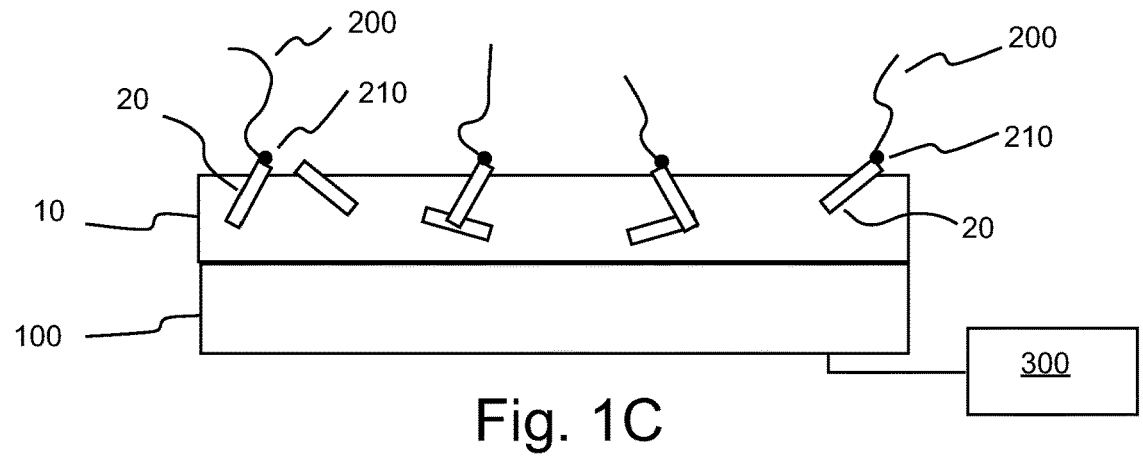
FIG. 1C illustrates schematically a conductive polymer and a GO dopant deposited on the surface of an electrode, with an agent bonded to the GO dopant.

FIG. 1C illustrates schematically a conductive polymer 10 and a GO dopant 20 after electropolymerization on the surface of an electrode 100. An agent 200 is illustrates as, for example, covalently attached to exposed GO dopant 20 via a linking group 210 which is the reaction product/residue of a functional group of the unreacted agent and a functional group of the unreacted GO. Agent 200 may also be attached via, for example, ionic bonding or sorption (for example, adsorption). The system of FIG. 1C further includes electronics of electronic circuitry 300 (illustrated schematically in FIG. 1C) in operative connection with electrode 100 which may, for example, include controllers, processors, analytical systems etc. as known in the electronics arts.

Figure 2:
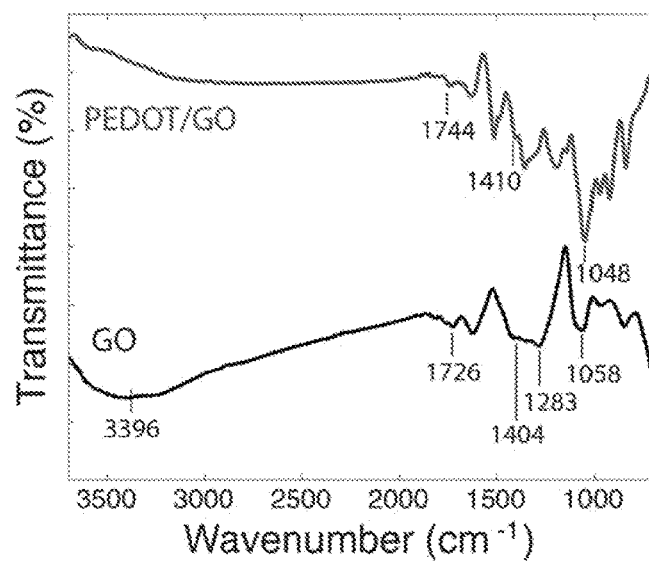
FIG. 2 illustrates FTIR spectra of GO sheets synthesized using a modified Hummers method (lower curve) and electropolymerized PEDOT film doped with GO sheets (upper curve).

FTIR analysis of the synthesized GO sheets and the PEDOT/GO films verified successful incorporation of GO into the film (see FIG. 2). Pure GO exhibits peaks at 3396 $cm^{-1}$, 1726 $cm^{-1}$, 1404 $cm^{-1}$, 1283 $cm^{-1}$, and 1058 $cm^{-1}$ that represent carboxylic O—H stretching and vibration, carboxylic C=O stretching and vibration, O—H deformation, epoxy C—O stretching and vibration, and alkoxy C—O stretching and vibration, respectively. The spectrum of the electrodeposited PEDOT/GO nanocomposite contains the characteristic peaks for C=O stretching and vibration of carboxyl groups at 1744 $cm^{-1}$ and O—H deformation at 1410 $cm^{-1}$. As PEDOT polymer does not contain either carboxyl or hydroxyl functional groups, the presence of such groups are attributable to GO, the sole dopant in the polymerization solution, indicating that the GO sheets have been successfully incorporated into the polymer film. The presence of the carboxylic carbonyl peak indicates that the film contains carboxylic acid functional groups provided by the GO sheets that may, for example, be utilized for agent (for example, bioactive agent/biomolecule) immobilization with, for example, carbodiimide crosslinking. The carboxylic O—H stretching and vibration band that should be apparent around 3400 $cm^{-1}$ is absent in the PEDOT/GO spectrum, and is likely obscured by the tail of the ~1 eV bipolaron absorption band, a typical attribute of conductive polymers PEDOT doped with various molecules, such as heparin, poly(styrene sulfonate), (PSS) and adhesive peptides has been shown to be relatively non-cytotoxic. However, soluble GO has demonstrated inconsistent toxicity effects. The biocompatibility of GO incorporated in conducting polymers has not previously been studied. To explore the cytocompatibility of the GO-doped conducting polymer film, the viability and death of neurons growing on the PEDOT/GO surface after 24 hours were evaluated with the MTT viability and propidium iodide (PI) exclusion assays and compared to PEDOT films containing the commonly and extensively studied dopant PSS. To isolate the effects of the polymer surface directly on the cell viability/death, the surfaces were not coated with laminin, an extracellular matrix protein widely used to promote neuron attachment and growth on various surfaces. There was no significant difference in viability between the PEDOT/GO and PEDOT/PSS films, with each group exhibiting greater than 96% of the metabolic activity of neurons growing on a control TCP surface (FIG. 3A). Neurons growing on the PEDOT/GO surface did not undergo a higher percentage of death than the cells on the PEDOT/PSS surface (GO: 12.79±5.0; PSS: 20.61±3.78, FIG. 3B).

A mechanism of soluble GO cytotoxicity shown in previous studies remains unclear, but multiple processes have been suggested, including uptake into the cell or adsorption onto the cellular membrane and consequent apoptosis or death, disruption of membrane integrity and cellular exchange, interference with cell adhesion, or induction of oxidative stress. Without limitation to any mechanism, the absence of significant cytotoxicity caused by PEDOT/GO films in the present studies may arise from the entrapment of the GO sheets within the film, hindering their ability to diffuse within the culture media and interact freely with the neurons. Cells growing on the surface of the film are largely contacting the PEDOT polymer, which has demonstrated biocompatibility with neuronal cells. The minimal toxicity of CP/GO materials such as PEDOT/GO films indicates that the nanocomposite materials have potential for biological/medical use (for example, as neural interfacing materials).

To evaluate the neural biocompatibility of the PEDOT/GO composite, films were electrochemically deposited on gold sputtered coverslips. The resulting PEDOT/GO coated coverslips were used as substrates to grow primary neuron cultures. SEM imaging revealed that neurons exhibited healthy growth on the surface of nanocomposite films in the absence of laminin treatment (FIG. 4). Cells spread and flattened on the film and extended long, highly branched neurites that interconnected with other neurons, demonstrating that the surface supported neural attachment and maturation. Possibly as a result of the specific network-like microstructure of the PEDOT/GO film, some of the smaller processes of neurons intimately grew along or around the partially exposed GO ridges on the surface of the film, potentially using the film morphology as a guidance cue for neurite outgrowth. Representative fluorescent images show neuron attachment and growth on PEDOT/GO and PEDOT/PSS films after 3 days in culture (see FIGS. 5A and 5B). The neurons grew on the surface of the PEDOT/GO film at a density comparable to that of PEDOT/PSS, indicating that the GO is not specifically contributing any obstruction to the attachment of cells (see FIG. 5C). While previous GO biocompatibility studies have indicated that GO initiates downregulation of adhesion proteins, such as laminin, fibronectin, and focal adhesion kinase-1, leading to a decrease in cellular adhesion, data from the present studies suggest that GO entrapped in the polymer matrix may not have such adverse effects on neuron attachment. These results agree with a proposed mechanism for decreased cell adhesion that attributes altered gene expression to the activation of intracellular pathways after GO nanoparticles adhere to the cell membrane. GO sheets embedded in the PEDOT polymer matrix may, for example, be restricted from interacting with the cell membrane in a way that would initiate changes in gene expression, rendering the PEDOT/GO film a favorable surface for cell attachment and growth.

Neurons growing on the PEDOT/GO film exhibited significantly longer neurites than cells growing on the PEDOT/PSS film (FIG. 5D, GO: 36.4±2.0 μm; PSS: 22.5±1.8 μm, p<0.01). Although the GO from the PEDOT/GO film is likely not being taken into the neuron cell body as a result of its entrapment within the polymer matrix, its ability to strongly physically adsorb proteins (which is a consequence of the huge surface area of its single-layer carbon structure) may attract components of the cell media to the surface of the polymer film, enhancing growth cone outgrowth. Additionally, neurons have been shown to be extremely responsive to a variety of topographical cues. In particular, surface roughness has been shown to promote neurite extension. The rough, network-like surface morphology of the PEDOT/GO film (FIGS. 1 and 4), compared to the smooth and featureless surface of PEDOT/PSS at the same scale may, for example, contribute to the longer neurite outgrowth in PEDOT/GO as compared to PEDOT/PSS. Regardless of the mechanism, the desirable effect on neurite outgrowth demonstrates that PEDOT/GO films are an amenable material for supporting neuronal growth and maturation, and may be useful substrates for neural tissue interfacing applications.

The GO sheets on the top layer of the PEDOT/GO films are partially embedded, as demonstrated by the network-like morphology of the film (see FIG. 1A-1C), and the exposed portions of the GO, rich in carboxyl groups (see FIG. 2), provide the PEDOT/GO films with many free functional groups. Utilizing carbodiimide conjugation to modify these functional groups, a method of bioactive agent/biomolecule patterning on conducting polymer films was demonstrated. In a number of representative examples, a laminin fragment peptide, p20, which is reported to promote neurite outgrowth, was conjugated to the electrodeposited film. The peptide was covalently attached to the PEDOT/GO film through the formation of amide bonds between the carboxyl groups on the surface of PEDOT/GO and the amine groups of the p20, with the assistance of crosslinkers EDC and NHS. The presence of p20 on the film after carbodiimide modification was verified by hydrolysis and amino acid quantification (5.37 pmol·mm$^{-1}$).

Figure 6A:
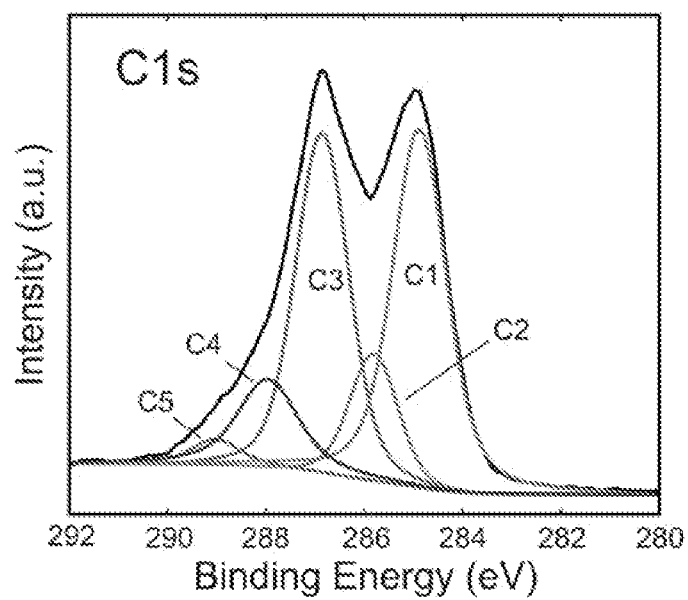
FIG. 6A illustrates high resolution XPS spectra of the PEDOT/GO surface after treatment with p20 in conjugation with EDC/NHS, showing deconvoluted peaks of the C1s region (C1: C—C; C2: C—O/C—S; C3: C—O—C; C4: N—C=O; C5: O—C=O).
Figure 6B:
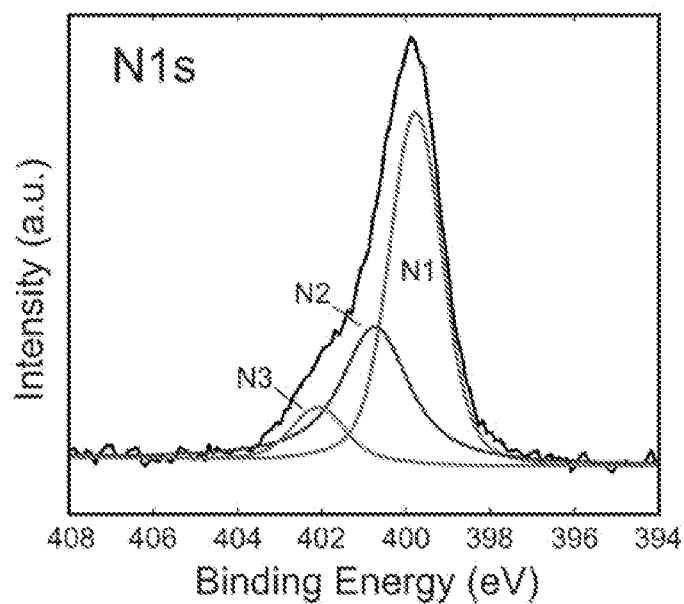
FIG. 6B illustrates high resolution XPS spectra of the PEDOT/GO surface after treatment with p20 in conjugation with EDC/NHS, showing deconvoluted peaks of the N1s region (N1: C—N; N2: N—C=O; N3: protonated amine).

XPS analysis of the PEDOT/GO film evaluated the surface chemistry of the film after p20 immobilization with EDC/NHS (see FIGS. 6A and 6B). The deconvoluted C1s region (FIG. 6A) consists of 4 peaks in addition to the main C—C peak located at 284.8 eV, including a C—O/C—S peak at 285.6 eV, an epoxy C—O—C peak at 286.9 eV, a N—C=O peak at 288.2 eV and an O—C=O peak at 288.8 eV. The PEDOT contributes to the C—S and C—O—C peaks, the GO sheets contribute to the C—O, C—O—C, and O—C=O peaks, and the peptide contributes to the O—C=O and N—C=O peaks. Analysis of the C1s region of the PEDOT/GO film treated with p20 in the absence of EDC/NHS resulted in a similar deconvolution. During the amide bond formation in the presence of EDC/NHS, a carboxylic acid provided by the GO reacts with an amine on the peptide, resulting in a net gain of one amide bond and a net loss of one carboxylic acid bond. However, since both the GO and peptide contain carboxylic acids, a comparison of the ratio of amide to carboxylic acid between the experimental groups cannot be used to verify the formation of covalent amide bonds between the peptide and the film with the addition of EDC/NHS. The carboxylic acid signal of the GO sheets is likely variable across the film depending on the proportion of GO exposed to the surface versus embedded within the polymer matrix, so the ratio of amide to carboxyl will not reflect the amount of covalently attached peptide. A more appropriate method of evaluating the amide formation is to monitor the ratio of amine to amide bonds. During the covalent reaction, one amine in the peptide p20 reacts with a carboxylic acid group to form an amide bond, so there will be more amide and less amine after the covalent treatment, as compared to the physical adsorption treatment. A high-resolution scan of the N1s region of the film treated with p20 and EDC/NHS revealed a peak centered at 388.9 eV, corresponding to the nitrogen in the peptide (FIG. 6B). Deconvolution of the N1s peak resulted in a C—N (amine) peak at amine peak at 401.8 eV. The amide/amine ratio is 0.58, compared to 0.19 in the absence of EDC/NHS crosslinking, indicating that the EDC/NHS treatment produced covalent linkages between the peptide and the PEDOT/GO film.

Figure 7A:
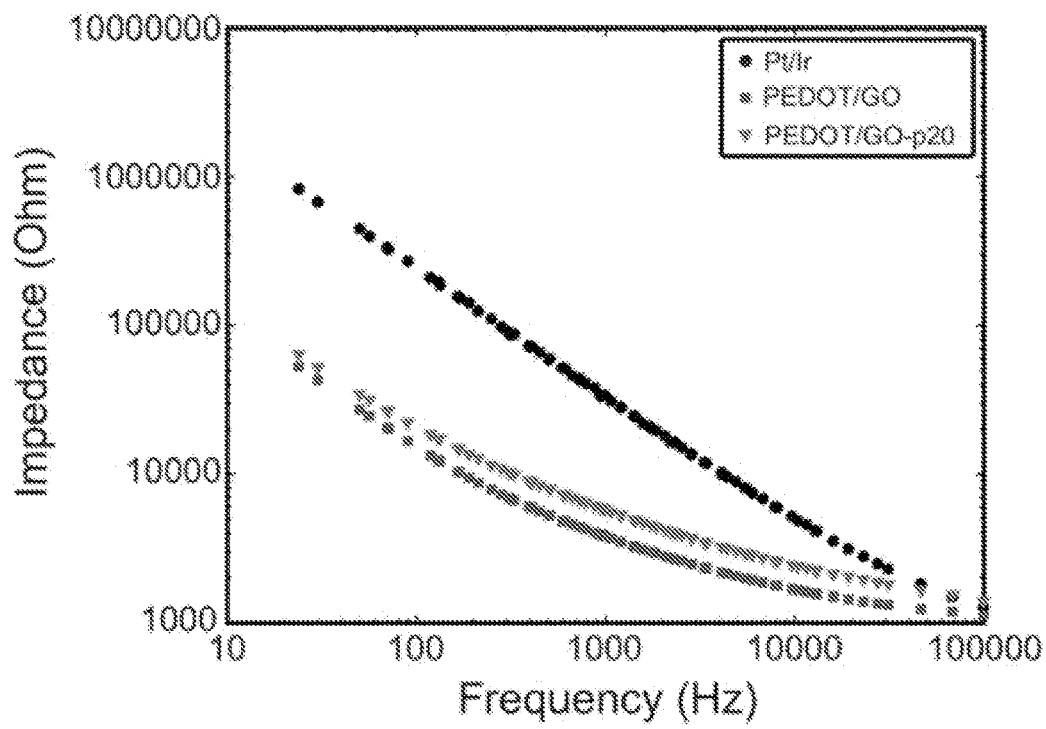
FIG. 7A illustrates Bode plots of the electrochemical impedance behavior of platinum iridium microwires: uncoated (circles), coated with PEDOT/GO (squares) and coated with PEDOT/GO covalently modified with p20 (triangles).
Figure 7B:
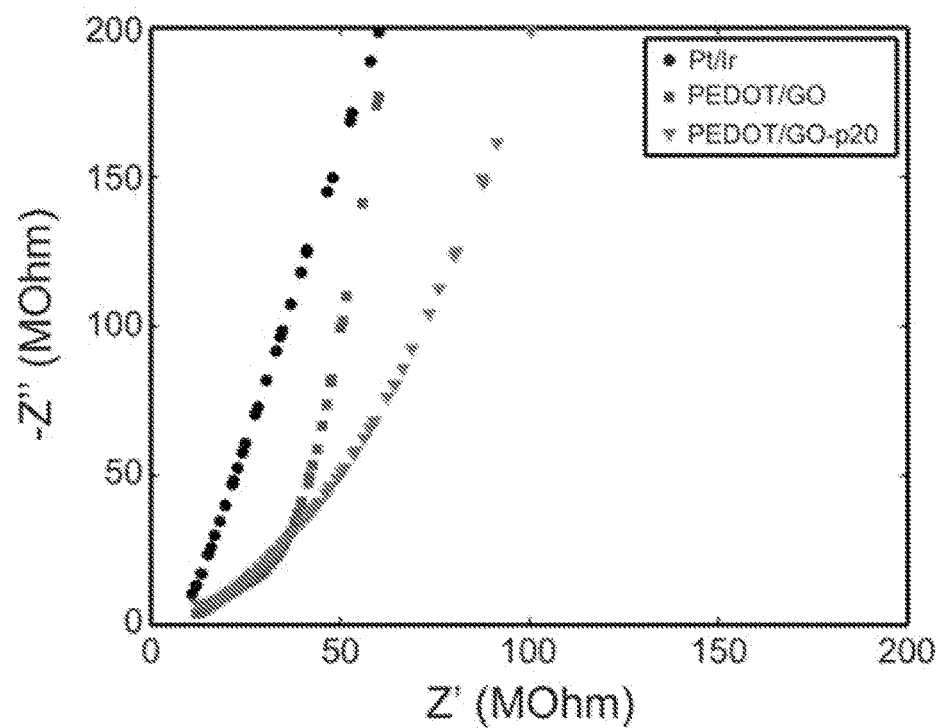
FIG. 7B Nyquist plots of the electrochemical impedance behavior of platinum iridium microwires: uncoated (circles), coated with PEDOT/GO (squares) and coated with PEDOT/GO covalently modified with p20 (triangles).

The electrical properties of the electrodeposited PEDOT/GO films before and after p20 immobilization were studied using EIS. As shown in FIG. 7A, coating the electrode with the PEDOT/GO film resulted in decreased impedance across all frequencies measured. Without limitation to any mechanism, the significant impedance decrease may, for example, be attributed to an increase in the effective surface area of the electrode as a result of the network-like surface microstructure of the nanocomposite polymer film. Longer deposition times resulted in a progressive decrease in impedance, demonstrating the film properties may be tuned as desired by controlling deposition parameters. At 1 kHz, a frequency relevant to single unit neural recording, the impedance is decreased by an order of magnitude after the PEDOT/GO deposition, indicating that the film may be a beneficial microelectrode coating to improve the recording and stimulation capability of neural electrodes. The Nyquist plot of the impedance (FIG. 7B) demonstrates that the bare metal has mostly capacitive behavior, as indicated by its steep linear curve. The electrodes coated with PEDOT/GO films exhibit a knee that separates capacitive behavior at low frequencies and diffusive behavior, characterized by a more gradual slope, at higher frequencies. The emergence of diffusion-dominated behavior may be attributed to the creation of a diffusion barrier by the conducting polymer film. After immobilization of p20 at the surface of the polymer film, the impedance increases slightly, a possible result of the creation of a nonconductive peptide layer at the electrode surface;

however, the impedance remains significantly lower than that of the bare metal electrode.

Figure 8A:
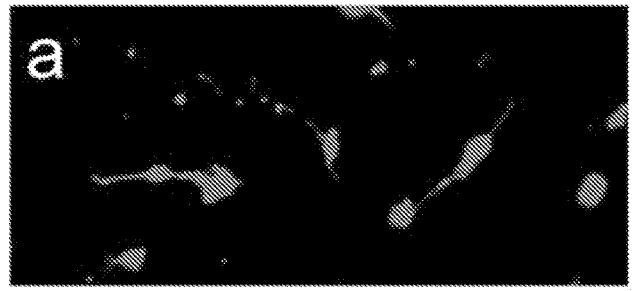
FIG. 8A illustrates neuron attachment and neurite outgrowth on PEDOT/GO surfaces modified with p20 peptide at 24 hours in a representative 20× fluorescent image of β-III-tubulin immunofluorescent reactivity of neurons cultured on a bare surface.
Figure 8B:
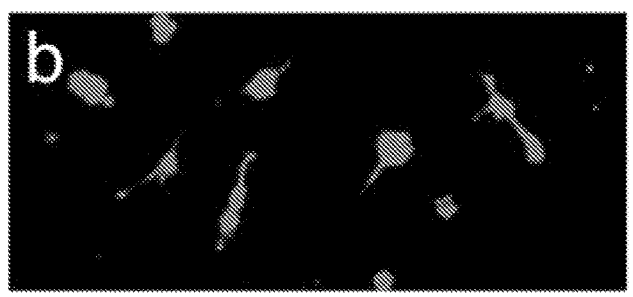
FIG. 8B illustrates neuron attachment and neurite outgrowth on PEDOT/GO surfaces modified with p20 peptide at 24 hours in a representative 20× fluorescent image of β-III-tubulin immunofluorescent reactivity of neurons cultured on a physically adsorbed p20 (p20 ADS) surface.
Figure 8C:
FIG. 8C illustrates neuron attachment and neurite outgrowth on PEDOT/GO surfaces modified with p20 peptide at 24 hours in a representative 20× fluorescent image of β-III-tubulin immunofluorescent reactivity of neurons cultured on a covalently immobilized p20 (p20 COV) PEDOT/GO surface (the scale bar represents 50 µm and is applicable to FIGS. 8A-8C).
Figure 8D:
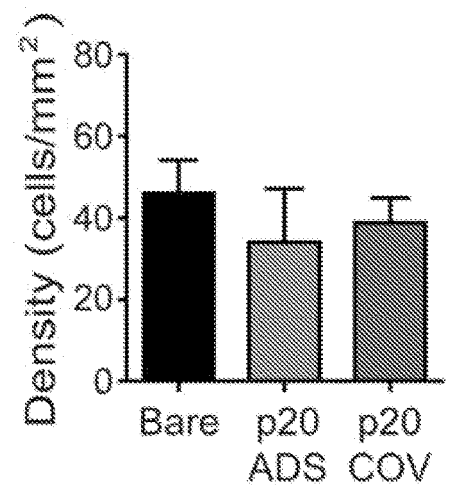
FIG. 8D illustrates neuron density (±SEM, n=3) growing on the p20 modified PEDOT/GO surfaces, showing that modification with p20 did not result in a change in cell density.
Figure 8E:
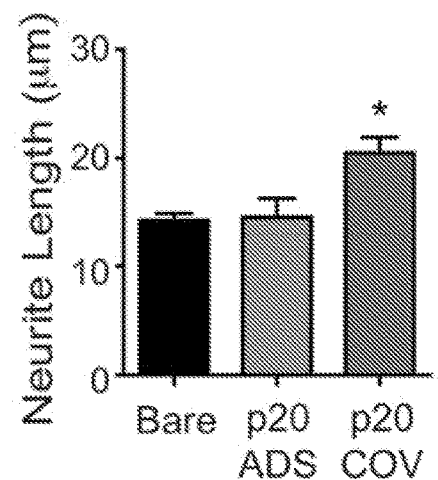
FIG. 8E illustrates average neurite length (±SEM, n=3) of neurons growing on the p20 modified PEDOT/GO surfaces (* $p<0.05$), showing that covalent immobilization, but not physical adsorption of p20 on the film surface enhanced neurite outgrowth.

The bioactivity of the immobilized p20 was assessed in representative studies with primary neuron culture on the functionalized PEDOT/GO films. After 24 hours in culture, neuron attachment and average neurite length were quantified and compared among PEDOT/GO films unmodified with peptide (bare), and films modified with p20 via physical adsorption or covalent immobilization. Representative fluorescent images illustrating β-III-tubulin immunoreactivity and neurite outgrowth on each film are shown in FIGS. 8A-8C. While there are no differences in the density of neurons attached to each film (FIG. 8D), the average neurite length (see FIG. 8E) of the neurons grown on the PEDOT/GO films covalently modified with p20 is significantly longer than that on the other two films (bare: 14.29±0.63 µm; adsorption: 14.59±1.72 µm; covalent immobilization: 20.48±1.45 µm, $p<0.05$). This observation may, for example, be ascribed to the effect of p20, which is the neurite outgrowth domain of laminin protein, and has been shown to enhance neurite outgrowth when incorporated into conducting polymer films as a dopant. In the studies, there was no discernable effect of p20 when physically adsorbed on the PEDOT/GO film. It is possible that the peptide did not retain its bioactivity, potentially as a result of conformational changes as a consequence of the physical adsorption onto the film that may obstruct laminin receptors on the neurons from binding to the peptide. Covalent anchoring of p20 to the PEDOT/GO film leaves most of the peptide free to interact with the cell, preserving the bioactivity of the peptide. It is also possible that the physically adsorbed peptide desorbs over the course of the cell culture experiment, resulting in less neurite outgrowth. The covalently conjugated p20 is very stable and continues to support neurite outgrowth after presoaking in PBS at 37° C. for 3 days prior to neuron culture (data not shown). This simple method of functionalizing GO doped CP materials such as PEDOT films with bioactive agents/biomolecules and its superior effectiveness over traditional biomolecule adsorption clearly demonstrates the potential of the nanocomposite materials hereof as a bio-interfacing material.

Electrodeposited CP/GO films showed good conductivity, and they can significantly lower the impedance of the coated electrodes. The CP/GO films possess a network-like surface structure as a result of the presence of partially embedded GO sheets. Further CP/GO composite materials support the growth of cells such as neurons with minimal toxicity. Partially exposed GO pieces on the surface of the CP/GO films are rich in free functional groups such as carboxyl groups, which offer the CP/GO films active functional groups for surface modification. In the representative embodiments discussed herein, a functional laminin peptide, p20, was bioconjugated to the surface of a PEDOT/GO film through a simple crosslinking reaction. However, that reaction and other that may be universally applied to a multitude CP/GO materials and bioactive agents. CP/GO materials thus provide excellent modifiability for use, for example, in biological and biomedical applications (for example, in neural interfacing and in biosensing).

In a representative embodiment of a sensor hereof, an analyte is detected via a sensor comprising a compound/moiety immobilized upon exposed GO in a CP/GO material which interacts with the analyte. In a number of embodiments, an enzyme is attached to GO in a CP/GO material to detect a substrate (the analyte) for the enzyme. For example, glutamate oxidase enzyme may be immobilized upon a CP/GO material (for example, PEDOT/GO), which is deposited upon an electrode, for the sensing of glutamate.

Figure 9A:
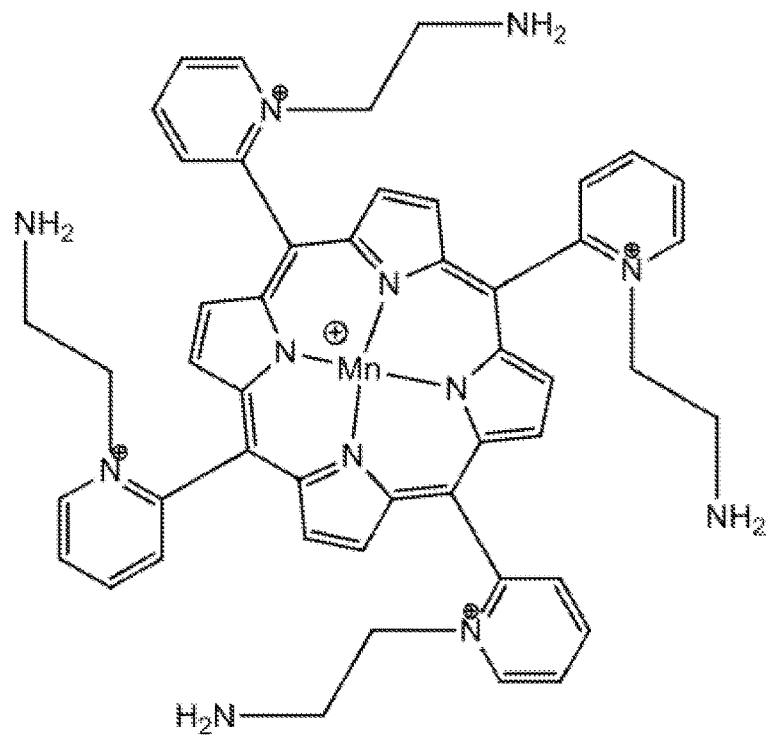
FIG. 9A illustrates an embodiment of a superoxide dismutase mimic (SODm).
Figure 9B:
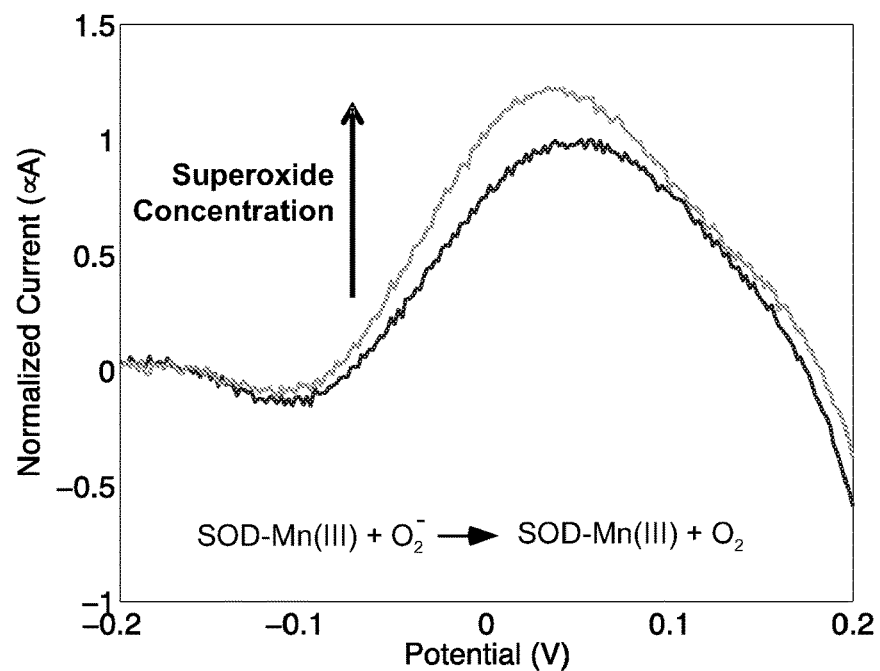
FIG. 9B illustrates that increased superoxide concentration results in a larger peak current when voltage of a sensor electrode including CP/GO with adsorbed SODm is swept past its oxidation potential.

Reactive oxygen species may, for example, be sensed using a CP/GO (for example, PEDOT/GO) material modified by physical adsorption of superoxide dismutase mimic (SODm). The SODm may alternatively be chemically (for example, covalently) bonded to the CP/GO composite material. An SODm is illustrated in FIG. 9A. SODm is an antioxidant metalloproteinase with a Mn core metal. The Mn is redox active and can be oxidized and reduced in response to a voltage sweep. This redox activity is the basis of the SODm antioxidant properties. In the presence of superoxide, the SODm will accept an electron, moving to its reduced state (see FIG. 9B), and converting the superoxide to oxygen. One can create a superoxide sensor by adsorbing the SODm onto the surface of the CP/GO film. When there is a larger amount of superoxide in a solution, there will be a larger amount of reduced SODm on the electrode, and when the voltage is swept past its oxidation potential, a larger peak current is observed (see FIG. 9B). Reactive oxygen specie may also be detected via, for example, a CP/OG composite including a physically adsorbed porphyrin such as hemin.

On-Demand Release of Immobilized Agents

On-demand release of an agent (for example, drug molecules from biomedical devices) enables precise, targeted application/dosing of the agent that can be temporally tuned to meet requirements for a variety of applications (for example, therapeutic applications). Recent advances have facilitated the use of various cues, such as UV- and visible-wavelength light, NIR radiation, magnetic field, ultrasound and electrical stimulation to trigger drug release in vivo from implanted smart materials. These techniques provide greater control over traditional in vivo drug release systems that rely on passive delivery that is programmed prior to implantation and cannot be modified in response to changing therapeutic needs. To achieve precise, controlled drug delivery, nanomaterial drug carriers are increasingly investigated because of their unique structures and tunable properties.

The huge surface area and $sp^2$ hybridized carbon lattice associated with carbon nanomaterials, such as carbon nanotubes, graphene, and graphene oxide (GO), enables highly efficient loading of agents such as drugs, while their capacity for modification provides a route to target agent/drug delivery and controllably release agents such as drug molecules. In a number of compositions hereof, an electrically controlled agent delivery system includes GO nanosheets incorporated into a conducting polymer (CP) film/matrix. The agent to be delivered is releasably immobilized within the film/matrix.

As described herein, nanocomposite films consisting of GO micro- or nanosheets and CPs demonstrate favorable electrical properties, good stability, neuronal biocompatibility and ease of surface modification with bioactive molecules. These properties, along with the low cost and simple synthesis of GO micro- or nanosheets (sometimes referred to herein collectively as nanosheets or simply sheets), make the GO/CP composite material/film an interesting candidate as a novel material for electrically controlled agent (for example, biologically active agent/drug) release.

Figure 10A:
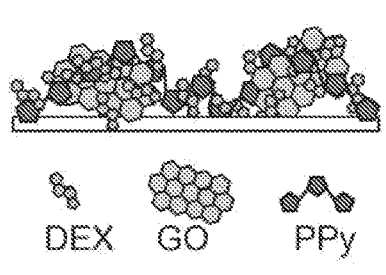
FIG. 10A illustrates a schematic representation of a DEX-loaded GO/PPy nanocomposite film.

During CP film polymerization, negatively charged species are typically loaded into the polymer matrix to balance positive charges formed on the backbone of the growing polymer. GO sheets are negatively charged as a consequence of carboxylic acid groups formed at their edges during the oxidation procedure, enabling them to be incorporated into the CP film as dopant molecules along with, for example, agents such as drug molecules (FIG. 10A).

In a number of representative embodiments, it was demonstrated that when incorporated into polypyrrole (PPy) along with anti-inflammatory drug, dexamethasone (DEX), GO nanosheets create a stable nanocomposite film that can release the drug molecules on-demand in response to electrical stimulation. In a number of studies, the DEX-loaded GO/PPy (GO/PPy-DEX) films were potentiostatically electrodeposited onto glassy carbon electrodes from a solution containing both GO nanosheets and DEX. During the electropolymerization reaction, the GO nanosheets compete with the anionic DEX as dopant molecules. Various factors, including molecule size and number of charges, may affect dopant incorporation into CP films. GO is a comparatively large structure with multiple negative charges, suggesting that it may not dope the film as readily as the smaller, more mobile DEX molecule that contains only two negative charges. Fourier-transform IR (FTIR) spectrum of the GO/PPy-DEX film displays peaks attributable to both GO and DEX, indicating that the drug molecules are successfully loaded into the film along with the nanosheets. The synthesized nanocomposite exhibited low impedance and high charge storage capacity, reflecting the favorable electroactivity of the film; as these properties decrease and increase, respectively, more current will pass through the film in response to a particular voltage pulse, enabling more efficient drug release.

Electrically controlled release of various agents, including biologically active agents/molecules may, for example, be achieved by utilizing the unique red-ox properties of GO/CP—releasable agent composite materials such the representative GO/PPy-DEX nanocomposite films hereof. In that regard, when the film is oxidized, negatively charged agents (for example, drug molecules) remain within the material to balance the positively charged polymer backbone. Reduction of the materials elicits the release of anionic dopant agents as the polymer backbone becomes neutrally charged.

Figure 10B:
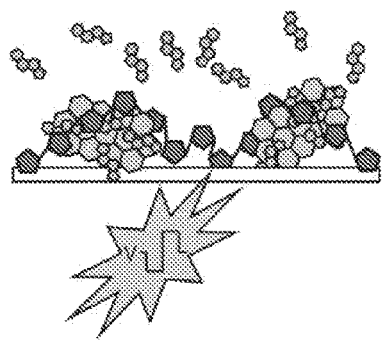
FIG. 10B illustrates a schematic representation of DEX release from the GO/PPy nanocomposite in response to electrical stimulation.
Figure 10C:
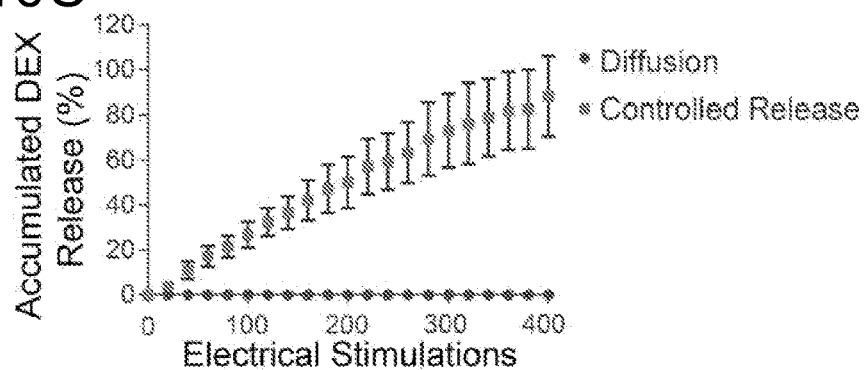
FIG. 10C illustrates a graph of cumulative release profiles of GO/PPy nanocomposite in response to electrical stimulation (n=3).
Figure 10D:
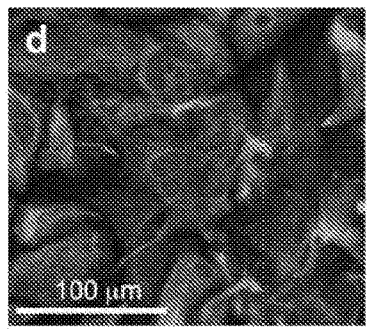
FIG. 10D illustrates a representative fluorescent image of astrocyte cultures exposed to no drug.
Figure 10F:
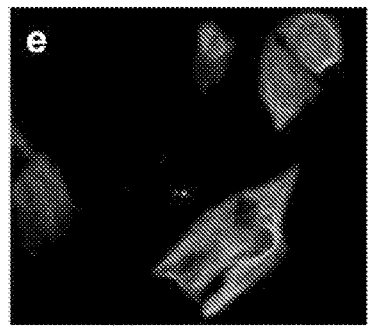
FIG. 10F illustrates a representative fluorescent image of astrocyte cultures exposed to prepared DEX solutions (DEX).
Figure 10E:
FIG. 10E illustrates a representative fluorescent image of astrocyte cultures exposed to DEX released from GO/PPy nanocomposite films (rDEX).
Figure 10G:
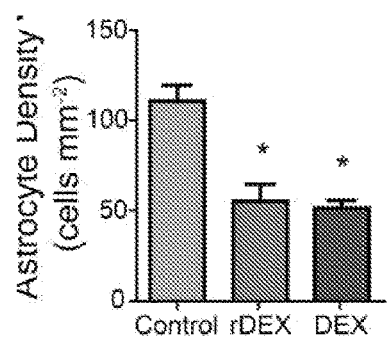
FIG. 10G illustrates a graph of the density of astrocyte cultures 4 days after exposure to drug treatment, wherein * indicates significant difference from control (n=4, p<0.05).

To evaluate its performance as a drug-releasing film, voltage pulses were applied through the GO/PPy-DEX nanocomposite immersed in PBS, and the release solution was analyzed with UV absorbance spectroscopy to quantify the amount of DEX expelled from the film. Application of negatively polarized voltage stimulation to the GO/PPy-DEX film initiated the release of DEX molecules from the film, while the GO nanosheets remained entrapped within the polymer matrix (see FIG. 10B). Large dopant molecules are generally immobile within CP films, suggesting that GO nanosheets, which may, for example, measure hundreds of nanometers to microns in the x-y direction, remain within the CP during film reduction. Small quanta of drug can be repeatedly released from the GO/PPy film in response to electrical stimulation (—0.5 V for 5 s followed by 0.5 V for 5 s in several representative embodiments), creating a drug release profile that is linear over several hundred stimulations. However, no observable drug passively diffused from the film in the absence of stimulation (see FIG. 10C). Moreover, there was no cracking or delamination of the GO/PPy film visible after undergoing repeated electrical stimulation, indicating that the nanocomposite has good electrochemical stability. The persistent linear release profile accompanied by good film stability is important, for example, in applications in which chronic, temporally precise drug dosing is required.

The bioactivity of the released representative drug was assessed by adding solutions containing DEX released from GO/PPy films to primary astrocyte cultures and evaluating the extent of interruption in cell proliferation. DEX is a synthetic glucocorticoid (GC) that is commonly used to treat inflammation and is used here as a model drug to demonstrate the capacity of the release system. Chronic DEX exposure has been shown to interrupt astrocyte proliferation, likely by downregulating glucocorticoid receptor expression. Astrocyte cultures exposed to the release solutions exhibited a significantly lower population of cells after 4 days of growth as compared to control cultures that received no drug treatment (FIGS. 10D-G, $p<0.05$). The cell density of the release solution-treated culture was not significantly different than that of a culture that was exposed to a prepared DEX solution at a known concentration of 1 µM. These data indicate that the process of incorporation into and electrically stimulated release from the nanocomposite film does not significantly alter the bioactivity of agents such as DEX molecules. To address the potential release of any toxic byproducts from the GO/PPy film, release solutions were applied to primary neuron cultures. No effect on neuron growth was visible after 2 days of exposure, indicating that the interruption of astrocyte growth was a result of specific actions of DEX, rather than non-specific cytotoxicity from components of the GO/PPy film (for example, monomer or GO nanosheets) that may have delaminated from the electrode during electrical stimulation.

During chemical synthesis of GO, oxidized graphite sheets are commonly exfoliated with ultrasonication to obtain single- and few-layer GO (s/fGO). During sonication, the sheets are also reduced in the x-y dimension to create a smaller particle size on the order of hundreds of nanometers. To investigate the effect of altering the GO nanosheet size on the properties of the nanocomposite, the GO suspension was submitted to 30 or 60 min of sonication immediately prior to incorporation into the film. When the GO suspension undergoes longer sonication treatment, the distribution of the nanosheet thickness shifts to smaller values, indicating that the sheets are exfoliated into more s/fGO sheets (see FIG. 11A). GO nanosheets may have enhanced utility as drug nanocarriers compared to other materials because their large surface area and $sp^2$ hybridized carbon structure enables efficient loading via adsorption of, for example, aromatic drug molecules, such as DEX. As multi-layer GO is exfoliated into thinner s/fGO particles, a larger amount of GO surface area is created within the suspension, supporting a higher level of agent adsorption onto the free GO nanosheets (FIGS. 11B and 11E).

Elemental analysis of the DEX-loaded nanocomposite films provides a semi-quantitative summary of the amount of drug loaded into the film. In that regard, each DEX molecule contains one fluorine atom and each subunit of PPy contains one nitrogen atom. Thus, the ratio of fluorine atoms to nitrogen atoms in the film corresponds to the amount of drug loading. As expected, nanocomposite films synthesized with GO sonicated for 60 min load more drug than the films synthesized with GO sonicated for 30 min, as indicated by the F:N ratio (FIG. 11c, $p<0.01$). Without limitation to any certain mechanism, FIG. 11E depicts the proposed mechanism by which controlling GO sonication time can tune drug loading into the polymerized nanocomposite, creating a level of flexibility that can meet the dosing needs of a particular application. The representative, drug-loaded GO/PPy nanocomposite may be electropolymerized from an aqueous solution containing free GO sheets and DEX molecules (and/or other agent(s)), creating an opportunity for the drug to load onto the surface of the nanosheets prior to film deposition. With more sonication treatment, more GO sheets are present in the polymerization suspension as each multi-layer GO particle is exfoliated into several s/fGO sheets. Prior to electrodeposition, the GO sheets load some DEX molecules onto their surfaces through physical adsorption, then compete with the remaining free DEX molecules as dopants during the polymerization reaction. As GO undergoes sonication, the nanoparticle size decreases in the z-direction (FIG. 11A) and the x-y-direction, creating smaller particles that act as more efficient dopant molecules. Additionally, as each multi-layered GO exfoliates into multiple s/fGO particles, there will be a larger number of interactive nanosheet edges containing negatively charged carboxylic acid groups. This should lead to more GO nanosheets depositing into the nanocomposite film, and because each GO sheet can carry multiple drug molecules into the film, a larger total amount of DEX can be loaded as a result of increased sonication treatment. Likewise, a larger amount of an agent may be immobilized upon exposed GO particles in the embodiment discussed above.

Interestingly, although increased GO sonication leads to more efficient drug loading into the nanocomposite, a significant change in the rate of DEX released from the film in response to voltage pulse stimulation was observed (FIG. 11D, $p<0.05$). After 100 stimulations, the nanocomposite synthesized with GO sonicated for 60 min released 38% less DEX than the 30 min sonication group. Without limitation to any mechanism, the strong adsorption of DEX molecules onto the GO sheets prior to deposition within the film may be the driving mechanism behind the slowed drug release rate (see FIG. 11E). It is possible that the DEX molecules adsorbed onto the GO surface cannot be as easily released from the film as directly doped DEX molecules as a result of the strength of the $\pi$-$\pi$ interactions, limiting the amount of drug release in response to the same electrical stimulation. Regardless of any underlying mechanism, the unique properties of the GO/CP composite materials such as GO/PPy nanocomposites may be utilized to create highly tunable release systems with the ability address various dosing needs for a multitude of agent delivery applications.

Along with providing control over drug loading and release, the GO nanosheets create a unique opportunity to alter the morphological characteristics of nanocomposite materials such as film. For example, sonication had a significant effect on the morphology of the DEX-loaded GO/PPy film (see FIG. 12A-12D). With less GO sonication, the film exhibited globular, cauliflower-like features on the scale of tens of microns that are characteristic of PPy films. As the amount of GO sonication increased from 30 min to 60 min, the large globular features flattened to create a more uniform surface (see FIGS. 12A and 12C). Without limitation to any mechanism, the large features are possibly a result of nucleation sites created by the multi-layer GO nanoparticles. As the nanoparticles deposit into the film, they may provide a scaffold around which the growing polymer can accumulate. With longer sonication time, the smaller s/fGO may distribute more evenly in the film, creating a smoother surface (FIG. 11E). At a smaller scale, as the sonication time increases, small sheet-like features became more apparent at the surface of the film, suggesting that more GO sheets were incorporated into the nanocomposite (see FIGS. 12B and 12D). At the 60 min sonication time point, the sheet-like features reduced in size to sub-micron dimensions, as would be expected because increased sonication treatment fractures GO sheets into smaller particles. The ability to subtly alter the nanocomposite surface morphology at different length scales may, for example, have important implications for applications in which the film interacts with tissue or cells. Multiple cell types have demonstrated sensitivity toward mechanical and topographical cues in their environment, suggesting that the nanocomposite film morphology may be engineered, for example, to act synergistically with the electrically controlled drug release to provide additional signals to the targeted cell population.

The GO sheets thus provide several degrees of customizability to the electrically controlled agent (for example, drug) release platforms hereof. By altering the size and thickness of the nanosheets, significant changes can be made to the film morphology, agent load and agent release properties. As a nanocarrier, GO enables loading of a variety of agents (including, for example, bioactive agents such as biomolecules), not limited to anionic species, into the materials (for example, films). Furthermore, the GO/CP nanocomposite materials exhibit a linear release profile that persists over many (for example, several hundred) stimulations, indicating that the release platform may be used in, for example, chronic drug release and other applications that require repeated release/dosing of an agent over time.

On-demand controlled drug delivery provides more effective therapies with less toxicity by tuning delivery directly to spatial and temporal requirements for a given application. In addition, controlled delivery may be beneficial in various in vitro assays, such as high-throughput drug screening or exploratory cell biology experimentation. Because of their adjustable properties, stability, and fine control over dosing, the GO nanocomposite release platforms described herein have the potential to advance such drug delivery technologies by enabling tailored drug release profiles over a range of dosage requirements.

Agents (including biologically active agents other than drugs) other than anionic agents may also be releasably immobilized within CP/GO composite materials hereof. For example, cationic species (for example, dopamine, acetylcholine, Na+, K+, Mg++ and Ca++) may be ionically bonded to the carboxylic acid groups on GO, or on an additional polyanion dopants. When a positive electrical current is applied, the negative species on the polyanion dopant or on the GO will interact with the conducting polymer backbone while cationic species will be released. For Zwitterionic molecules, it is possible to adjust the media pH and push the molecules to either negative or positively charged. For neutral molecules releasably immobilized or entrapped within a CP/GO composite material hereof, it is possible to force or "squeeze" the neutral agent out of the CP/GO composite material as a result of electrical actuation of the CP/GO films. For example, electrically induced oxidation and reduction always accompany ionic and water movement in or out of the film, which leads to shrinkage and expansion. Such volumetric and porosity change can be used to allow entrapped molecules to be released.

EXPERIMENTAL EXAMPLES

Materials. Graphite powder was purchased from Bay Carbon Inc. (SP-1, Bay City). 3,4-Ethylenedioxythiophene (EDOT), poly(sodium-4-styrenesulfonate) (PSS, Mw~70,000), phosphate buffered saline (PBS, pH 7.4, 10 mM sodium phosphate and 0.9% NaCl), glutaraldehyde (25% in $H_2O$), osmium tetroxide (0s04, 4 wt. % in $H_2O$), hexamethyldisilazane (HMDS), 1-Ethyl-3-(3-dimethylaminopropyl)carbodiimide (EDC), and N-Hydroxysuccinimide (NHS) were purchased from Sigma-Aldrich. The peptide RNIAEIIKDI (p20) was synthesized at the University of Pittsburgh Peptide Synthesis Facility. All other chemicals were of analytical grade, and Milli-Q water from a Millipore Q water purification system was used throughout.

Electrodeposition. GO was synthesized through the oxidization of graphite powder according to the modified Hummers method, and characterized using transmission electron spectroscopy (TEM) (JEOL JEM-2100F). The Hummers method is, for example, described in W. S. Hummers and R. E. Offeman, *J Am Chem Soc*, 80, 1339-1339 (1958) and N. Mohanty and V. Berry, *Nano Lett*, 2008, 8, 4469-4476, the disclosure of which are incorporated herein by reference. PEDOT/GO films were electrodeposited onto platinum/iridium (Pt/Ir) microelectrodes (standard tip, diameter: 2-3 μm, MicroProbes, Gaithersburg, Md.) for electrochemical characterization or gold sputtered plastic microscope coverslips (macroelectrode area: 0.38 cm$^2$) for surface characterization and cell culture using a Gamry Potentiostat, FAS2/Femtostat (Gamry Instruments, Warminster, Pa.) with Gamry Framework software. A conventional three-electrode system with the Pt/Ir or gold electrode acting as the working electrode, a platinum foil as the counter electrode, and a silver/silver chloride (Ag/AgCl) reference electrode (CH Instruments, Austin, Tex.) was used. The PEDOT/GO was electropolymerized from an aqueous solution containing 0.02 M EDOT and 10 mg/mL GO. PEDOT/PSS films were synthesized from an electropolymerization solution containing 0.02 M EDOT and 0.1 M PSS. A constant potential of 1.0 V was applied to achieve a charge density of 200 nC total for microelectrodes or 100 mC/cm$^2$ for macroelectrodes.

Modification of PEDOT/GO with p20. The peptide p20 was covalently immobilized on the surface of the PEDOT/GO coated electrodes through an amine reaction between carboxyl groups on the GO and amine groups on the peptide. The PEDOT/GO electrodes were incubated in a solution of 0.2 mg/ml p20, 0.2 M EDC and 0.2 M NHS in sterile H$_2$O for 3 h at room temperature, and then thoroughly washed with sterile PBS to remove any free p20, EDC or NHS. In another set of samples, PEDOT/GO films were incubated with p20 in the absence of EDC/NHS as a control for physical adsorption. The amount of p20 on the surface of the covalently modified PEDOT/GO film was quantified using amino acid hydrolysis followed by high performance liquid chromatography.

Electrochemical Impedance Spectroscopy. The electrochemical impedance spectroscopy (EIS) was measured with an Autolab potentiostat/galvanostat, PGSTAT128N (Metrohm Autolab) with Nova 1.8 software using a three-electrode system with a platinum foil counter electrode and Ag/AgCl reference electrode. The EIS was measured in PBS in the frequency range from 10 Hz to 100 kHz using an alternating current sinusoid of 20 mV in amplitude with the direct current potential set to 0 V.

PEDOT/GO Film Surface Analysis. The surface of PEDOT/GO films was characterized using Fourier transform infrared (FTIR) spectroscopy, scanning electron microscopy (SEM) and x-ray photoelectron spectroscopy (XPS). FTIR measurements were carried out using a Bruker Vertex 70 spectrometer equipped with a Hyperion 2000 microscope. A 20× attenuated total reflectance (ATR) objective was employed to record the spectra of deposited thin films. The ATR spectra were converted to transmittance spectra via the standard method within the spectrometer operation software package, OPUS 6.5.

The surface morphologies and microstructures of the PEDOT/GO films were examined with an XL30 SEM (FEI Company) operated at 10 kV. Samples with neurons growing on the surface were analyzed with the same SEM, but at a lower operating potential of 5 kV. Samples with cells were treated with 2.5% glutaraldehyde and 1% OsO4, both for one hour in sequence, followed by dehydration. The dehydration was performed by soaking the samples in 30% and 50% ethanol in PBS, 70% and 90% ethanol in water, and 100% ethanol in sequence for 15 min each, followed by immersion in HMDS for 15 min.

XPS analysis of PEDOT/GO films after treatment with p20 in the presence or absence of EDC/NHS was performed with a K-Alpha XPS system (Thermo Scientific) equipped with a monochromated A1 $K_\alpha$ source (1486.68 eV). High resolution scans of the C1s and N1s regions were taken at two locations on each sample.

Primary Neuron Culture. PEDOT/GO coated macroelectrodes were fixed to the surface of 24-well culture plates with Kwik-Sil (World Precision Instruments) and sterilized with exposure to UV light for 15 min. Following sterilization, the polymer surfaces were washed with sterile PBS. Cortical tissue was isolated from E18 Sprague-Dawley rat embryos and treated with 0.025% Trypsin in a digestion buffer containing 137 mM NaCl, 5 mM KCl, 7 mM Na$_2$HPO$_4$, and 25 mM HEPES. Neurons were dissociated with gentle trituration and maintained in Neurobasal medium (Invitrogen, 21103-049) supplemented with B27 (Invitrogen, 17504-044), GlutaMax (Invitrogen, 35050-061) and Antibiotic-Antimycotic (Invitrogen 15240-062). For neuron growth assays, cells were seeded on PEDOT/GO and PEDOT/PSS surfaces at a density of 100k cells per electrode and grown for 3 days. For neuron viability and death assays, polymer samples were cut to fit into 96-well plates and seeded with neurons at a density of 10k per well. For the cell cultures intended to assess the p20 functionalization on PEDOT/GO films, similar procedures were followed. In order to measure the neurite length easily by preventing the formation of very long and interconnected neurites, neurons were seeded on the PEDOT/GO surfaces at a density of 100k cells per electrode and grown for only 24 h before fixation and immunocytochemical analysis.

Immunofluorescence Staining and Quantification. Neurons growing on the polymer surfaces were fixed in 4% paraformaldehyde in PBS for 15 min and washed several times with PBS. The cells were immersed in a blocking buffer (5% goat serum/0.2% triton-X in PBS) for 20 min followed by incubation in mouse monoclonal antibody against β-III-tubulin (TuJ1, 1:1000, Sigma) for 1 h. After washing in PBS, the cells were incubated in goat anti-mouse Alexa Fluor 488 (1:1000, Invitrogen) secondary antibody for 1 h, washed in PBS and counterstained for nuclei using Hoechst 33342 (Invitrogen).

TuJ1-immunoreactive cells were imaged using a fluorescence microscope. For each experimental group, 10 random 10× images were collected from each sample (n=3). Neuron density was quantified by counting the number of TuJ1-immunoreactive cells that extended at least one neurite that measured longer than the width of the cell body. Neurite analysis was performed using the NeuronJ plugin for ImageJ (a public domain JAVA® language image processing program) downloadable from the Unites States National Institutes of Health. Neurites extending from each TuJ1+ cell body were traced and measured, and the average neurite length was calculated.

Neuron Viability and Toxicity Assay. The viability of neurons growing on the PEDOT/GO composite and PEDOT/PSS films, as indicated by their mitochondrial activity, was assessed with the MTT Cell Proliferation Assay Kit (Molecular Probes). The ratio of absorbance signal at 570 nm to 630 nm (reference wavelength) was used to assess metabolic activity. All polymer samples were normalized to a blank containing the polymer sample with no cells, and compared to a positive control containing cells growing on the tissue culture polystyrene (TCP) well surface.

Percentage of cell death was assessed using the propidium iodide (PI) assay. PI fluoresces after binding to the nuclear material of dead cells, while the plasma membrane of healthy cells excludes the dye. Polymer samples were prepared and neuron culture performed as in the MTT assay. Fluorescence was evaluated in a spectrometer with an excitation at 530 nm and emission at 618 nm. Polymer samples were normalized to controls containing the same polymer with 100% dead cells, and compared to cells growing on the TCP control surface.

Electrochemical Apparatus. All electrochemical experiments were performed with a Gamry Potentiostat, FAS2/Femtostat (Gamry Instruments) using a three-electrode set-up with glassy carbon (GC) working electrodes (3 mm diameter, CH Instruments), a platinum wire coil counter electrode, and a silver/silver chloride reference electrode (CH Instruments).

Nanocomposite Film Synthesis. As described above, GO was synthesized by the modified Hummers method as previously described. PPy films were electrochemically synthesized on the GC electrodes from an aqueous solution containing 0.2 M pyrrole (Sigma-Aldrich) and 10 mg ml$^{-1}$ dexamethasone 21-phosphate disodium salt (DEX, Sigma-Aldrich) and GO nanosheets (5 mg ml$^{-1}$). The GO suspension was ultrasonicated for 30 min immediately prior to electropolymerization, unless otherwise noted. A constant potential of 0.8 V was applied until the charge density reached 400 mC cm$^{-1}$.

Film Characterization. The surface morphology and microstructure was evaluated with scanning electron microscopy (SEM, JEOL JSM6510). Film surface chemistry was evaluated with attenuated total reflectance Fourier transform IR (ATR-FTIR, Bruker Vertex 70). Elemental analysis was performed by energy-dispersive X-ray spectroscopy (EDS, Oxford INCA EDS). Film roughness ($R_a$) and GO nanosheets thickness were evaluated with atomic force microscopy (AFM, Bruker Dimension V SPM).

Electrically Controlled Drug Release. All drug release experiments were carried out in PBS. Films were submitted to square-wave biphasic voltage pulses of −0.5 V for 5 s followed by 0.5 V for 5 s. The PBS solutions containing the released drug were analyzed with UV spectroscopy at a wavelength of 242 nm to quantify the amount of DEX release. To determine total amount of drug release, films underwent aggressive voltage pulses (−2 V for 5 s followed by 0 V for 5 s) until cumulative drug release plateaued. This value was used to calculate percentage of drug release reported in FIG. 11D.

DEX Loading Capacity Assay. The amount of DEX loaded on GO sheets was evaluated by incubating 100 μM DEX with 0.5 mg ml$^{-1}$ GO in H$_2$O for 2 h at room temperature. Prior to incubation with DEX, the GO suspension was sonicated for 30 min or 60 min. The mixture was centrifuged for 30 min at 14,000 RPM to pellet the DEX-loaded GO nanosheets, and the supernatant was analyzed with UV spectroscopy at 242 nm to determine the amount of DEX remaining in solution. The amount of drug loaded was calculated by subtracting the amount of free DEX in the supernatant from the amount of DEX in a sample not incubated with GO.

Bioactivity Assay. To determine the bioactivity of released DEX, astrocyte cultures were exposed to release solutions for 4 d then fixed and immunostained for glial fibrillary acidic protein (GFAP). Detailed cell culture and immunofluorescence methodology are described in the supporting information.

Statistical Analysis. All statistical analyses were carried out in SPSS software. Student's t-tests were utilized for comparisons of two experimental groups and one-way analysis of variance (ANOVA) tests followed by Bonferroni's post hoc analysis or Tukey's post hoc analysis were utilized for comparisons of more than two experimental groups. Statistical significance was considered for $p<0.05$ (*) and $p<0.01$ (**). All data is presented as the mean (±SEM).

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A composition, comprising:
    a support; and
    a composite material electrodeposited upon the support, the composite material comprising at least one polymer including contiguous sp$^2$ carbon centers, the polymer being doped solely with a graphene oxide composition to increase conductivity in the polymer, wherein the graphene oxide composition comprises graphene oxide and at least one agent immobilized upon graphene oxide, the at least one agent being immobilized on the graphene oxide in an arrangement selected from at least one of (i) on the graphene oxide extending from the surface of the composite material or (ii) within the composite material; and wherein the polymer is doped either by (i) electropolymerizing monomers for the polymer in the presence of the graphene oxide wherein the support functions as an electrode during electropolymerization, wherein the at least one agent is immobilized upon the graphene oxide after polymerization or (ii) by electropolymerizing monomers for the polymer in the presence of the graphene oxide composition wherein the support functions as an electrode during electropolymerization.

2. The composition of claim 1 wherein the at least one agent is immobilized on graphene oxide extending from the surface of the composite material.

3. The composition of claim 2 wherein the at least one agent is chemically bonded to the graphene oxide or adsorbed on the graphene oxide.

4. The composition of claim 3 wherein the at least one agent is covalently bonded or ionically bonded to the graphene oxide.

5. The composition of claim 1 wherein the at least one agent is releasably immobilized within the composite material.

6. The composition of claim 5 wherein the at least one agent may be controllably released from within the composition via application of electrical energy thereto.

7. The composition of claim 2 wherein the at least one agent is an anionic agent, a cationic agent, a zwitterionic agent or a neutral agent.

8. The composition of claim 2 wherein the at least one agent is a biologically active agent.

9. The composition of claim 8 wherein the biologically active agent comprises at least one of a biomolecule or a drug.

10. The composition of claim 8 wherein the biologically active agent comprises an amphetamine, a steroid, an anesthetic, an analgesic, an antacid, an antibiotic, an anticoagulant, an antidepressant, an antidote, an antihistamine, an antiinflammatory, an antimycotic, an anticancer agent, an analgesic agent, an antirejection agent, an antiretroviral, an antiviral, a barbiturate, a beta blocker, a booster, a contraceptive, a decongestant, a depressant, an emetic, an expectorant, a hypnotic, an immunosuppressant, a laxative, a narcotic, a neurochemical, an opiate, a painkiller, a prophylactic, a purgative, a relaxant, a sedative, a statin, a suppressant, a tranquilizer, a vaccine or a vitamin.

11. The composition of claim 8 wherein the biologically active agent comprises a superoxide dismutase mimic, a porphyrin, a protein, an organic catalyst, a nucleic acid, an organometallic, a glycoprotein, a glycosaminoglycan, a peptide, an aptamer, a polyamine, a polyamino acid, a cytokine, a carbohydrate, an oleophobic, a lipid, extracellular matrix, a component of extracellular matrix, a growth factor, a hemostatic agent, a virus, a vireno, a virus vector, or a prion.

12. The composition of claim 8 wherein the biologically active agent comprises a cell adhesion molecule, an adhesive protein, a peptide, a cytokine or a growth factor.

13. The composition of claim 8 wherein the biologically active agent comprises an aptamer, an antibody, an enzyme, a ribozyme, DNA or RNA.

14. The composition of claim 8 wherein the biologically active agent is dexamethasone.

15. The composition of claim 2 wherein the at least one polymer is selected from the groups of polypyrroles, polyanilines, poly(3,4-ethylenedioxythiophene), poly(fluorine)s, polypyrenes, polyazulenes, polynaphthalenes, polycarbazoles, polyindoles, polyazepines, poly(p-phenylene sulfide), polythiophenes, poly p-(phenylene vinylene), poly p-phenylene, and their derivatives.

16. A method of forming a composition including a support and a composite material electrodeposited upon the support, the composite material including at least one polymer including contiguous sp2 carbon centers, comprising:
doping the polymer solely with a graphene oxide composition to increase conductivity in the polymer, wherein the graphene oxide composition comprises graphene oxide and at least one agent immobilized upon graphene oxide, the at least one agent being immobilized on the graphene oxide in an arrangement selected from at least one of (i) on the graphene oxide extending from the surface of the composite material or (ii) within the composite material; and wherein doping the polymer comprises either (i) electropolymerizing monomers for the polymer in the presence of the graphene oxide wherein the support functions as an electrode during electropolymerization, wherein the at least one agent is immobilized upon the graphene oxide after polymerization or (ii) by electropolymerizing monomers for the polymer in the presence of the graphene oxide composition wherein the support functions as an electrode during electropolymerization.

17. The method of claim 16 wherein the graphene oxide extends from the surface of the composite material and the method further comprising:
immobilizing the at least one agent upon the graphene oxide extending from the composite material.

18. The method of claim 17 further comprising:
controlling particle size of the graphene oxide to control at least one property of the composition.

19. The method of claim 18 wherein the at least one conducting polymer is polymerized in the presence of graphene oxide.

20. A method, comprising:
providing a composition, the composition comprising a support and a composite material electrodeposited upon the support, the composite material comprising at least one polymer including contiguous sp2 carbon centers, the polymer being doped solely with a graphene oxide composition to increase conductivity in the polymer, wherein the graphene oxide composition comprises graphene oxide and at least one agent releasably immobilized upon graphene oxide, the at least one agent being immobilized on the graphene oxide in an arrangement selected from at least one of (i) on the graphene oxide extending from the surface of the composite material or (ii) within the composite material; and wherein the polymer is doped either by (i) electropolymerizing monomers for the polymer in the presence of the graphene oxide wherein the support functions as an electrode during electropolymerization, wherein the at least one agent is immobilized upon the graphene oxide after polymerization or (ii) by electropolymerizing monomers for the polymer in the presence of the graphene oxide composition wherein the support functions as an electrode during electropolymerization, and applying an electric current to the composition to release the agent from the composite material.

* * * * *